United States Patent [19]

Nakayama

[11] Patent Number: 4,468,948
[45] Date of Patent: Sep. 4, 1984

[54] METHOD AND APPARATUS FOR MEASURING THE CONCENTRATION OF A GASEOUS OR VOLATILE SUBSTANCE IN A LIQUID

[75] Inventor: Takehisa Nakayama, Takasago, Japan

[73] Assignee: Kanegafuchi Kagaku Kogyo Kabushiki Kaisha, Osaka, Japan

[21] Appl. No.: 357,324

[22] Filed: Mar. 11, 1982

[30] Foreign Application Priority Data

| Mar. 11, 1981 | [JP] | Japan | 56-34796[U] |
|---|---|---|---|
| Mar. 11, 1981 | [JP] | Japan | 56-34797[U] |
| Mar. 11, 1981 | [JP] | Japan | 56-34798[U] |
| Apr. 6, 1981 | [JP] | Japan | 56-51972 |
| Apr. 6, 1981 | [JP] | Japan | 56-50076[U] |
| Apr. 20, 1981 | [JP] | Japan | 56-56880[U] |
| Apr. 20, 1981 | [JP] | Japan | 56-56881[U] |
| Apr. 27, 1981 | [JP] | Japan | 56-62348[U] |
| Apr. 27, 1981 | [JP] | Japan | 56-62349[U] |
| Apr. 30, 1981 | [JP] | Japan | 56-66304 |
| May 9, 1981 | [JP] | Japan | 56-69709 |
| May 11, 1981 | [JP] | Japan | 56-71127 |
| Jun. 5, 1981 | [JP] | Japan | 56-83404[U] |
| Jun. 5, 1981 | [JP] | Japan | 56-83405[U] |
| Jun. 5, 1981 | [JP] | Japan | 56-83406[U] |

[51] Int. Cl.$^3$ .............................................. G01N 7/10
[52] U.S. Cl. ....................................... 73/19; 55/158
[58] Field of Search ................. 73/19, 23, 23.1; 55/158, 270

[56] References Cited

U.S. PATENT DOCUMENTS

| 3,087,112 | 4/1963 | Pfefferle | 73/23.1 |
|---|---|---|---|
| 3,879,984 | 4/1975 | Welland | 73/23.1 |
| 4,257,257 | 3/1981 | Dairaku et al. | 73/19 |

OTHER PUBLICATIONS

Kazuo Dairaku & Tsuneo Yamane, "Use of the Porous Teflon Method to Measure Gaseous or Volatile Substances Dissolved in Fermentation Liquids", Biotechnology and Bioengineering, vol. 21, 1979, pp. 1671-1676.

Primary Examiner—Stephen A. Kreitman
Attorney, Agent, or Firm—Armstrong, Nikaido, Marmelstein & Kubovcik

[57] ABSTRACT

An apparatus and method for measuring the concentration of a gaseous or volatile substance in a liquid, which comprises passing a carrier gas through a liquid-repellent porous partition tubing, immersed in a liquid, having continuous minute channels extending through the tubing wall, introducing to a gas detector the gaseous volatile substance passing from the liquid into the carrier gas through the continuous minute channels while controlling the flow rate and the pressure of the carrier gas by simultaneously operating both a carrier gas control means and a choking means. Also disclosed is a method for the measurement of the same which is equipped with sterilization, calibration and standby function so that it may be immediately applied to an actual industrial scale process including cultivation of microorganisms, brewing and the like. Further disclosed are various measuring apparatus for the practicing of the foregoing methods. Porous partition tubing made of tetrafluoroethylene resin is used having an average pore size of about 0.1 to 1.0 μm and a porosity of about 20 to 80%. The carrier gas is controlled to produce a specific pressure difference under certain conditions.

42 Claims, 42 Drawing Figures

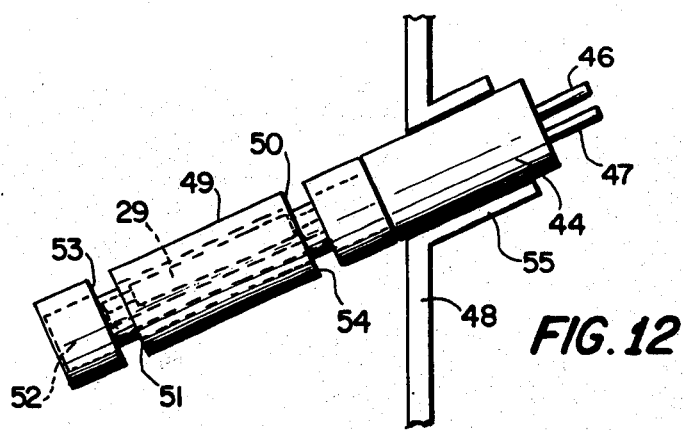
FIG. 12
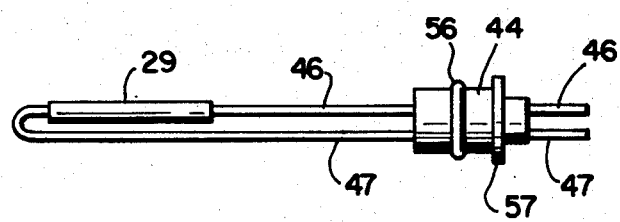
FIG. 15-A
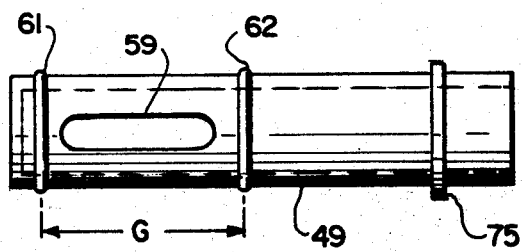
FIG. 15-B
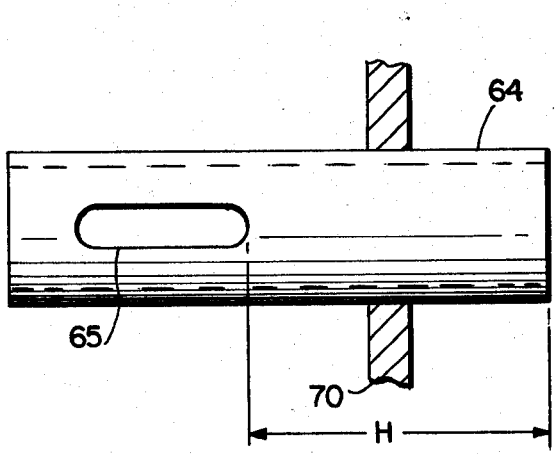
FIG. 15-C
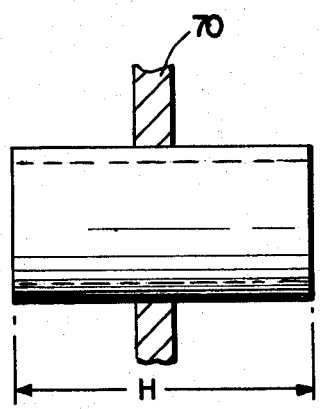
FIG. 15D

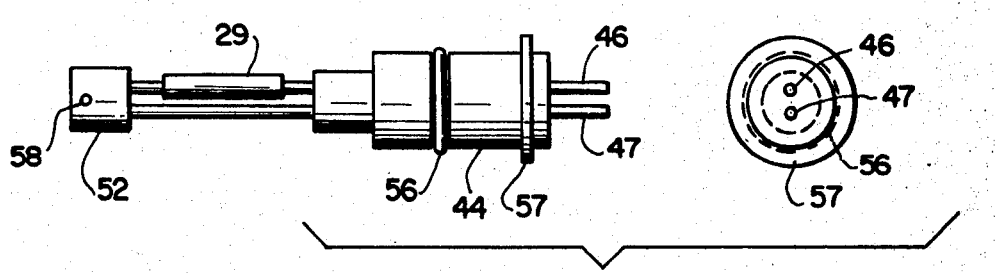
FIG. 13-A
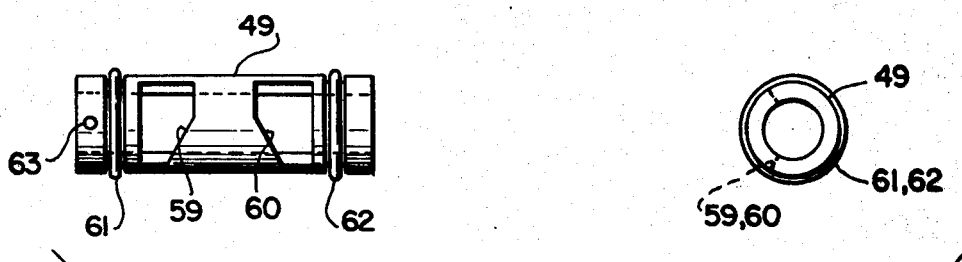
FIG. 13-B
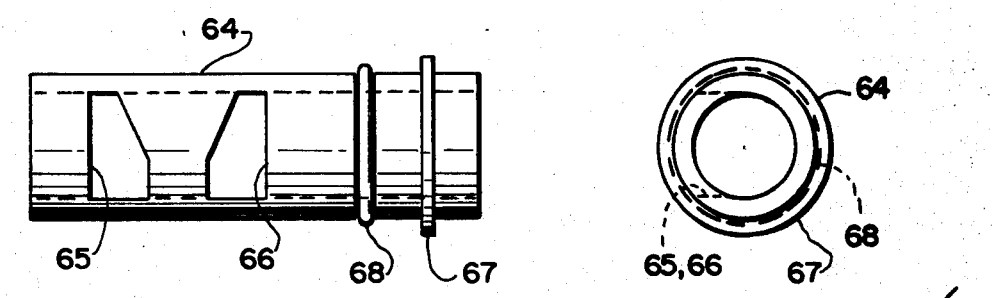
FIG. 13-C
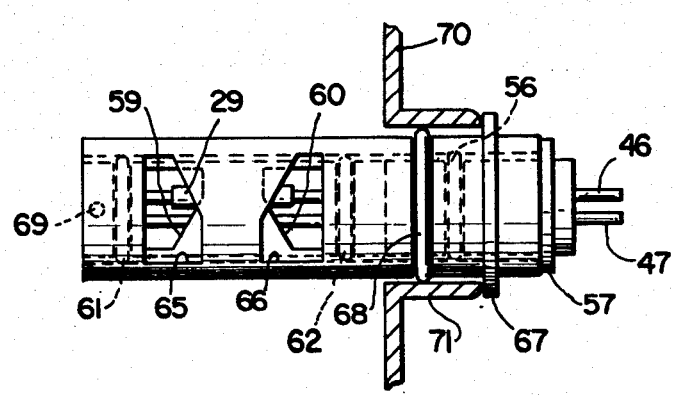
FIG. 13-D

METHOD AND APPARATUS FOR MEASURING THE CONCENTRATION OF A GASEOUS OR VOLATILE SUBSTANCE IN A LIQUID

BACKGROUND OF THE INVENTION

1. Field of the Invention

The present invention relates to a novel and useful method and apparatus for rapidly and accurately measuring the concentration of a gaseous or volatile substance in a liquid. More particularly, it relates to and apparatus and method for measurement of the concentration of a gaseous or volatile substance in a liquid which can be suitably applied in industrial processes wherein measurement for an extremely long period of time and highly reliable results are required under conditions of violent flow and deep spots of the liquid.

2. Description of the Prior Art

A method and appararus measurement of the concentration of a gaseous or volatile substance is disclosed by U.S. Pat. No. 4,257,257 which is comprised of a sampling device (sampler) for sampling of a gaseous or volatile substance in a liquid using a liquid repellent porous partition tubing having continuous minute channels and a detector of the foregoing substance. In this U.S. Patent, a basic method and apparatus for the measurement of the concentration of the gaseous or volatile substance is taught, which comprises the steps of immersing a liquid repellent porous partition tubing having continuous minute channels extending through the wall of the tubing into a liquid to be tested, connecting a carrier gas supply pipe to one end of the tubing and a carrier gas discharge pipe to the other end, passing a given amount of carrier gas through the tubing, leading the carrier gas to a detector, detecting the quantity of the gaseous or volatile substance permeating through the tubing wall from the liquid and diffusing into the carrier gas, thereby measuring the concentration of the substance in the liquid continuously or intermittently.

The invention revealed by said U.S. Patent is only concerned with a fundamental principle of the measurement method, materials of the porous partition tubing employed and a basic and general method and apparatus. In this sense, it may be safely said that it is not always suitable for a practical industrial scale, but feasible tentatively on a beaker scale in the laboratory. That is, it is usable under relatively mild measurement conditions where properties of the liquid to be tested are suited to the tubing material, pressure imposed on the tubing is relatively small since, on a beaker scale, flow of the liquid is considerably mild, depth of the liquid is shallow, the measurement is effected in an open system and continuous measurement time is fairly short, for example, several tens of hours, and the like. As a matter of fact, when the measurement method and apparatus based on the principle as aforesaid is applied on an industrial scale to, for example, a fermentor used in cultivation processes of microorganisms, various problems arise and have to be solved. More concretely, even with, for example, a fermentor of microorganisms in which the measuring conditions are considered to be relatively mild, various problems are encountered when the foregoing method and apparatus for measuring gaseous or volatile substances in liquids employing a porous partition tubing having liquid repellency and continuous minute channels is adopted.

(1) The culture broth, in which various nutrients including predominantly inorganic salts and dissolved materials, shows an interfacial tension in the neighborhood of 40 dyne per cm even at a standard cultivation temperature of 30° C., and sometimes shows as low as 37 dyne per cm, depending on the kind of the desired microorganisms.

(2) As a rule, in a practical process the volume of the liquid tested i.e., culture broth is great, the depth of the liquid sometimes 7 or 8 m, depending on the shape of the fermentor and the value of gas hold up. Accordingly high pressure is imposed on the sampler.

(3) Microorganisms are generally cultivated batchwise, especially be fed-batch method in most cases. As a result, the amount of the liquid increases with the lapse of time, in consequence, the depth of the liquid also increases with time.

(4) The cultivation of microorganisms is carried out by two different ways. One is a so-called anaerobic cultivation requiring no oxygen and the other is a so-called aerobic cultivation necessitating oxygen. When obtaining products contained by cells, by-products by cells or products contained in cells, aerobic cultivation is commonly conducted. In this case, a great amount of oxygen or oxygen-containing gas i.e., air is allowed to jet out through a plurality of nozzles having a minute diameter from a lower portion of the fermentor to thus uniformly disperse air bubbles in the culture broth, while, if required, circulating the culture broth by mechanical agitation. Furthermore, to improve dissolution of oxygen into the culture broth, it is occasionally practiced to position a choking means to an air exhaust line from the fermentor, thereby maintaining the inside pressure of the fermentor at rather increased pressure by the operation of the choking means.

(5) Not only continuous cultivation, but batch cultivation usually undergoes along-period cultivation, occasionally continuous measurement being required over 100 hours.

In summing up the foregoing problems, it is said that the culture broth has no properties suitable for the porous tubing of liquid repellency and continuous minute channels, because of its low interfacial tension in particular. Even if the porous tubing having pore size and porosity adaptable for the interfacial tension is properly selected, when the porous tubing is positioned to the fermentor and the measurement is effected, considerably great liquid pressure is imposed on the tubing coming from the depth of the liquid and pressurizing operation of the entire cultivation system. For the reasons, the interfacial tension of the liquid and the liquid pressure permit the liquid to permeate through minute channels. That is, in fact, fatal to the method for measurement of gaseous or volatile substances in liquids by the use of the porous partition tubing having liquid repellency and continuous minute channels. On the other hand, when the porous tubing is selected which has pore size and porosity enough to prevent the liquid from permeating through the minute channels, resisting the pressure imposed on the tubing, the passageway of gaseous or volatile substances permeating from the liquid into the carrier gas i.e., the total amount of continuous minute channels, reduces correspondingly, thereby leading to a decreased amount of gaseous or volatile substances permeating, with a result that said gaseous or volatile substances in the carrier gas passing through the porous tubing and the liquid to be tested do not reach gas-liquid equilibrium. That is also an obstacle to the utilizaton of the foregoing method.

In an attempt to reach the gas-liquid equilibrium, the surface area of the porous tubing has to be provided adequately, which means an increase in diameter and length of the porous tubing. Hence, the portion of the sampler immersed in the liquid to be tested increases. That gives rise to a disadvantage that the porous tubing is liable to suffer from damage and undesirable influences due to flow of the liquid.

In addition. in application of the foregoing measurement method to the practical process, there are problems as set below;

(6) The cultivation process of microorganisms requires a high degree of sterilization. For this purpose, not only the fermentor per se, but detectors of various measuring devices should have all such a construction that liquids are difficult to remain and that washing and sterilization are feasible. Prior to cultivation they are subjected to strict sterilization. The sterilization is normally performed by two ways; sterilizaton by the use of chemicals and thermal sterilizaton. It is common that various detectors are positoned to the fermentor, then the entirety of the fermentor is sterilized at 120° C. to 130° C. by heating under pressure.

The sampler of gaseous volatile substances in liquids providing the liquid repellent porous tubing having continuous minute channels should have also such a construction as permitting no residue of liquids, facilitating washing and sterilization and standing sterilization by heating under pressure by the use of steam of 120° C. to 130 C.

(7) Different from the measurement on a beaker scale, the sampler, one installed to the practical fermentor, can be neither inspected nor exchanged. In the culture broth of microorganisms, there are contained various impurities including adhesive substances, in particular. These and cells adhere to the surface of the porous tubing during the course of cultivation for a prolonged period of time and, what is worse, cause blocking of minute channels. As a result, a decrease in sensitivity of the measurement or impossibility of the measurement is unavoidable.

As in apparent from the foregoing, the measurement method and apparatus using a porous partition tubing having liquid repellency and continuous minute channels disclosed by the U.S. Pat. No. 4,257,257, when applied to the measurement of the concentration of gaseous or volatile substances in liquids on a practical industrial scale process, involves a variety of problems to be solved.

For instance, when gaseous or volatile substances in a culture broth having the interfacial tension of approximately 40 dyne per cm are measured using a porous tubing made of tetrafluoroethylene resin having an average pore size of about 0.45 $\mu$m, a porosity of about 60%, a thickness of about 500 $\mu$m, an inside diameter of about 3 mm and an outside diameter of about 4 mm, which is found to be most preferable in respect of a liquid repellent porous tubing having continuous minute channels and exhibiting a superior sensitivity and strength, the culture broth starts to permeate through the minute channels of the tubing in only several hours to several tens of hours after the commencement of measurement, when the depth of the liquid is about 3 m, the measurement being thus hindered. Moreover, the foregoing tubing is placed in a steam sterilization atmosphere elevated at 120° C. to 130° C., the porous tubing is wholly deformed by the outside pressure to thus collapse. Further, the inside of the porous tubing and a carrier gas discharge pipe is filled with steam permeated through the continuous minute channels of the porous tubing and water resulting from condensed steam. When stains or plugging occur, it is next to impossible, on an industrial process, to make inspection or replacement, as was stated earlier.

SUMMARY OF THE INVENTION

It is therefore a primary object of the present invention to improve a measurement method and apparatus disclosed by the U.S. Pat. No. 4,275,275 and to provide a method and apparatus for measuring a gaseous or volatile substance in a liquid a porous partition tubing having liquid repellency and continuous minute channels which can be suitably applied with high reliability to an actual industrial process wherein continuous measurement for an extremely prolonged period of time is demanded under severe conditions including violent liquid flow and deep measuring spots and the like.

A first object of the present invention is to provide a measurement method and apparatus which enables the continuous measurement for about 100 hours of the concentration of a gaseous or volatile substance in a fermentor in which microorganisms are cultivated with violent flow of liquid under slightly increased pressure.

A second object of the present invention is to provide a measurement method and apparatus using the porous tubing which suffers from no damages or adverse effects by sterilization treatment commonly practiced in the cultivation process, thus affording accurate measurement.

A third object of the present invention is to provide a measurement method and apparatus using the porous tubing which is capable of calibration so that without removing a sampler including the porous tubing, positioned to a practical process, it is possible to know at any time outputs measured of the liquid to a liquid of a known concentration.

A fourth object of the present invention is to provide a measurement method and apparatus using the porous tubing which is equipped with standby system against sudden uexpected damages, end of the lifetime and decrease in the sensitivity of the porous tubing during the course of measurement.

A fifth object of the present invention is to provide a sampler involving the porous tubing which facilitates replacement, inspection and washing of the porous tubing during the course of measurement.

A sixth object of the present invention is to provide a porous tubing and a sampler which can stand violent flow of the liquid to be tested and high pressure.

These and other objects of the present invention together with the advantages thereof will become apparent to those skilled in the art from the detailed disclosure as set forth hereinbelow.

BRIEF DESCRIPTION OF THE DRAWINGS

FIG. 12 is a diagram illustrating the installation of a sampling means to the wall of a container.

FIG. 13 is a diagram indicating a sampling means in a double-cylinder construction with a variable opening for measurement wherein (A) depicts a sampler body, (B) is an inner cylinder, (C) is an outer cylinder and (D) indicating the installation of the sampling means to the wall of the container.

DETAILED DESCRIPTION OF THE INVENTION

Figure 1:
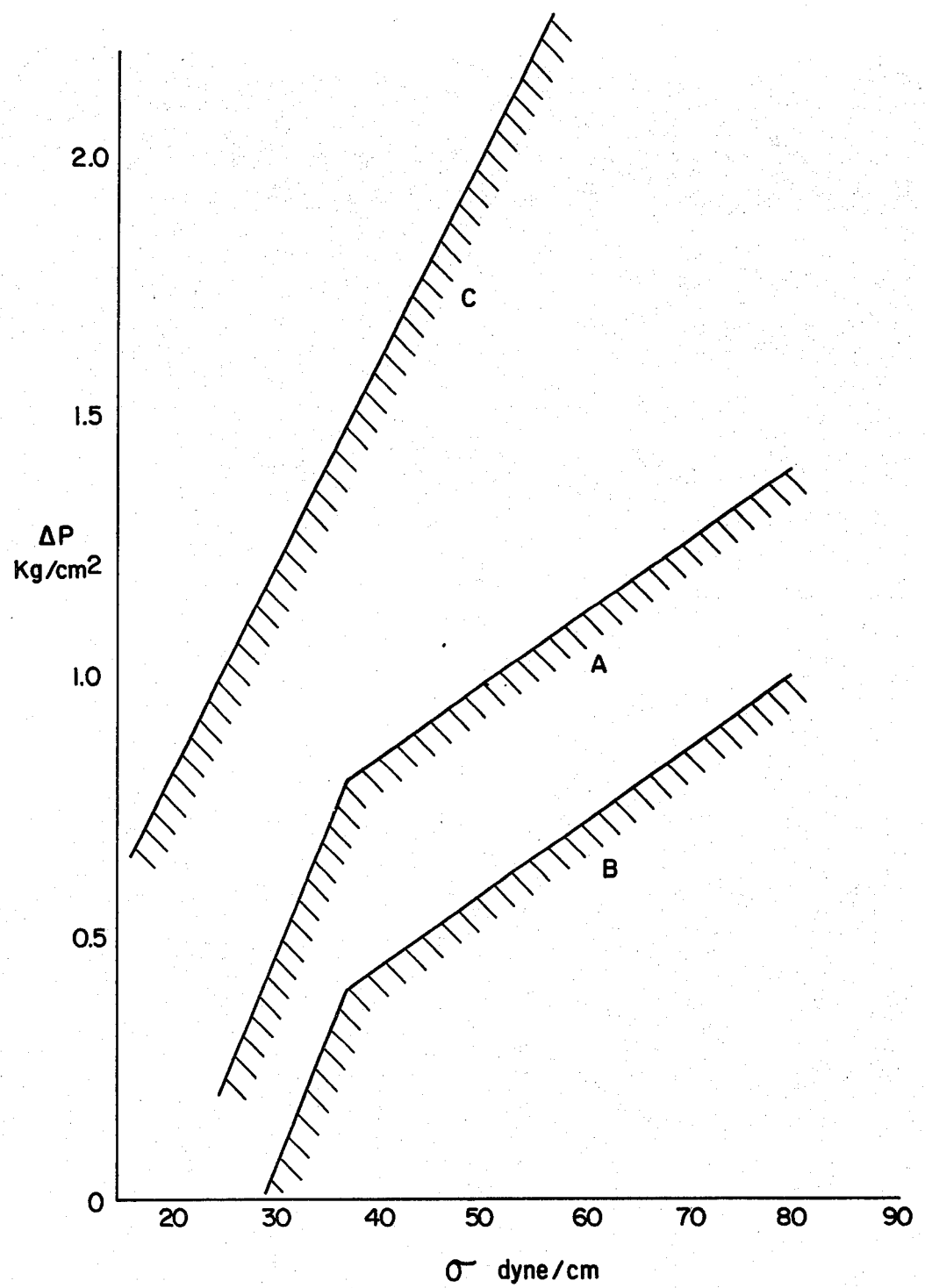
FIG. 1 is a graph showing the range of the pressure difference between liquid pressure and carrier gas pressure inside the tubing to the interfacial tension of the liquid to realize the long-term continuous measurement.

The basic principle of a measurement method using a porous partition tubing having liquid repellency and continuous minute channels extending through the wall of the tubing is described as below. Hereinafter, the porous partition tubing having liquid repellency and continuous minute channels extending through the wall of the tubing is referred to as "a porous tubing". Moreover, the porous tubing to both ends of which a carrier gas supply pipe and a carrier gas discharge pipe are connected, respectively, is referred to as "a sampler".

In the application of the foregoing measurement method, it is most important to prevent a liquid to be tested from permeating through the continuous minute channels of the porous tubing. The permeation of the liquid through the continuous minute channels of the porous tubing is determined by a material of the tubing, a pore size, properties of a liquid to be tested, pressure of the liquid imposed on the porous tubing and the like. The pressure difference ΔP between respective sides of the porous tubing is defined as below.

ΔP=(pressure of the liquid to be tested in contact with the porous tubing)—(pressure of the carrier gas passing through the porous tubing)

The permeation of the liquid through the continuous minute channels takes place theorethcally when the following equation is satisified.

$$\Delta P \geq 0.02 \cdot \sigma \cdot \cos\theta/R \ (Kg/cm^2) \quad (1)$$

wherein $\sigma$ is the interfacial tension (dyne per cm), $\theta$ is the contact angle (rad.) between the liquid to be tested and the material of the tubing, R is the pore size ($\mu$m).

As a matter of fact, however, the measurement sometimes becomes infeasible because of the permeation of liquid through the continuous minute channels within a short time, even when $\Delta P < 0.02 \cdot \sigma \cdot \cos\theta/R$ (Kg per $cm^2$) is satisfied. It has been found that liquids containing impurities, colored substances and adhesive substances like a culture broth containing molasses as the substrate cause especially the permeation of the liquid through the continuous minute channels, since stains of those substances adhere with a lapse of time to the surface of the porous tubing.

The present inventors have made an extensive studies on the relation among the time until the permeation of the liquid through the continuous minute channels i.e., continuously measurable time, the interfacial tension $\sigma$ of the liquid and the pressure difference ΔP, using the porous tubing made of tetrafluoroethylene resin, which is found to be the most suitable in respect of measurement of volatile substances in liquids and the strength of the tubing, having a pore size of about 0.45 $\mu$m, a porosity of about 60%, a thickness of about 500 $\mu$m, an inside diameter of about 3 mm and an outside diameter of about 4 mm. As a result, it has become apparent that the greater the interfacial tension of the liquid is, the more becomes the resistance of the tubing to the pressure difference, and that when the interfacial tension is the same, continuously measurable time becomes longer as the pressure difference nears zero. The relation between $\Delta P$ (Kg per cm$^2$) and the interfacial tension $\sigma$ (dyne per cm) of the liquid in which 30 to 50 hour-continuous measurement is feasible is in the range shown by A in FIG. 1. This range is also described by the following equations.

In the case of $$37 \geq \sigma \geq 25, \Delta P \leq 0.05\sigma - 1.05 \qquad (2)$$

In the case of $$\sigma > 37, \Delta P \leq 0.0143 - +0.27 \qquad (3)$$

It has also been found that the range of $\Delta P$ enabling a long-term continuous measurement for over 50 hours is in the range shown by B in FIG. 1. Likewise, by the following equations it is defined.

In the case of $$37 \geq \sigma \geq 29, \Delta P = 0.05\sigma - 1.45 \qquad (4)$$

In the case of $$\sigma > 37, \Delta P \leq 0.0143\sigma - 0.129 \qquad (5)$$

The range depicted by C in FIG. 1 indicates the range of $\Delta P$ where the permeation of the liquid into the porous tubing does not occur theoretically, as shown by the equation (1). It is understood from FIG. 1 that for the long-term continuous measurement the range of $\Delta P$ should be maintained much smaller than that theoretically permitting the liquid to permeate through the continuous minute channels.

Another experiment has been made using a tetrafluoroethylene porous tubing having a different pore size, as to the relation between the pressure difference $\Delta P$ (Kg per cm$^2$) and the pore size R ($\mu$m) which is capable of continuous measurement for 30 to 50 hours, it has been discovered that $\Delta P$ is proportion to a reciprocal of R. That is, the relation between $\Delta P$ and R is generally defined as below;

When the interfacial tension $\sigma$ (dyne per cm) is between 37 dyne per cm and 25 per cm, $$\Delta P = (0.025\sigma - 0.5)/R \text{ (Kg/cm}^2\text{)} \qquad (6)$$

When $\sigma$ is more than 37 dyne per cm, $$\Delta P = (0.0072\sigma + 0.135)/R \text{ (Kg/cm}^2\text{)} \qquad (7)$$

Needlessly, these equations are obtained experimentally and thus they are not always applied to every case without exception. It is therefore preferred to select $\Delta P$ in a safer value according to the foregoing equations. It is also needless to say that the pressure difference $\Delta P$ should preferably be the smallest value in the range as aforesaid. Care must be taken that the pressure difference $\Delta P$ should not be too small to thus cause negative pressure, namely, the carrier gas pressure exceeds the liquid pressure. That is because the carrier gas jets out into the liquid through the continuous minute channels of the porous tubing so that the amount of flow of the carrier gas passing through the porous tubing varies, affording an adverse effect on the measurement and reducing the accuracy.

Moreover in the porous tubings there are included not a few tubings having irregular pore sizes or having no pore sizes according to the specification on account of an error in manufacturing. From this viewpoint as well, it is an important point to maintain the pressure difference $\Delta P$ as near as zero for the long-term stable measurement.

Although the point for the long-term stable measurement using the liquid repellent porous tubing is made clear, it is rather difficult to apply the foregoing to a practical process. That is, to prevent the liquid pressure from being exerted on the porous tubing, the sampling means including the porous tubing has to be positioned near the surface of the liquid. Otherwise, the liquid is taken out and led to the sampling means located in such a way that substantially no liquid pressure is imposed on the porous tubing. In the former case, there may arise a problem that in a batch process varying the amount of liquid with time or a process accompanied by the violent flow of liquid or up-to-down movement of liquid, the porous tubing is not exposed to or in contact with the liquid. In the latter case, there is a drawback of delay in the measurement since the liquid has to be taken out for measurement from the container. The latter case is also undesired because in a process such as the cultivation of microorganisms requiring a high countermeasure to contamination of miscellaneous microorganisms, the shape of the fermentor and the discharge line become complicated, so that adequate sterilization is not carried out.

Taking into full consideration these problems, it is considered optimum to increase the pressure inside the porous tubing, i.e., the carrier gas pressure with a view to reducing the pressure difference $\Delta P$ between the liquid and the inside the tubing.

Notwithstanding, the conventional measurement method revealed by the U.S. Pat. No. 4,275,275 pays attention to the uniform control of the amount of flow of the carrier gas in spite of sensitivity and accuracy and, as far as the carrier gas pressure is concerned, attention is drawn only to not jetting out of the carrier gas in the liquid through the continuous minute channels and uniform stable amount of flow of the carrier gas.

In the detectors the carrier gas is normally discharged into the atmosphere and the flow rate of the carrier gas is in a small amount of several tens ml per min, and hence the carrier gas exiting from a flow control means has nearly no pressure. Accordingly the pressure of the carrier gas passing through the porous tubing approaches the vicinity of zero.

With the use of a tetrafluoroethylene porous tubing having a pore size of about 0.45 $\mu$m, a porosity of about 60%, an inside diameter of 3.0 mm, an outside diameter of 4.0 mm, a length of 100 mm and a thickness of 500 $\mu$m, the optimum flow rate of the carrier gas is approximately 40 ml per min, whereas in the conventional apparatus when the carrier gas is passed at a rate of about 40 ml per min. through a carrier gas supply pipe the carrier gas pressure inside the porous tubing comes up close to zero. With such the conventional apparatus, when the carrier gas pressure is increased slightly, the flow rate of the carrier gas is increased exceedingly to thereby greatly exceed the optimum flow rate of the carrier gas. In such the apparatus it is impossible to achieve the carrier gas supply concurrently satisfying desired amount of flow and pressure in the porous tubing.

When the carrier gas pressure is increased at the upstream of the porous tubing, the flow rate is immediately increased. Nonetheless when a suitable resistance is positioned at the downstream against the flow, the carrier gas becomes difficult to flow for the increased pressure at the upstream and thus the flow rate, in itself, is not so increased. That is, even when the carrier gas of slightly high pressure is supplied at the upstream of the porous tubing, the resistance, for example, a choking means located at the downstream maintains an optimum flow rate while preventing an increase in the amount of the carrier gas. In conclusion, to control the flow rate and the pressure of the carrier gas passing through the porous tubing to a desired and optimum value, it is necessary to operate at the same time the carrier gas control means located to the upstream and the choking means located to the downstream.

The pressure, or the lowest pressure when variable at the measuring point is detected or seized, then the carrier gas pressure passing through the porous tubing is controlled by the adjustment of the carrier gas control means and the choking means to the liquid pressure to be tested or the permissible range of the pressure difference from the lowerest pressure when variable, and concurrently the flow rate being also controlled to a desired and optimum value.

In the cases where the pressure of liquid to be tested is constant, a desired and optimum pressure difference between the liquid to be tested and the carrier gas partitioned by the porous tubing wall is obtained by various methods including, for example, the employment of a resistance pipe having a predetermined pressure loss, a detector having a predetermined pressure loss as the carrier gas discharge pipe per se up to the detector, the detector per se having a predetermined pressure loss or any combination of the foregoings. Of course, the carrier gas discharge pipe at the downstream of the porous tubing and the line up to the detector possess a considerable resistance respectively and thus if it is adequate for the desired flow rate and pressure of the carrier gas, no specific choking means is required. Moreover it is also effective to select the carrier gas discharge pipe at the downstream and the detector such that a desired flow rate and pressure be provided at the portion of the porous tubing.

Figure 2:
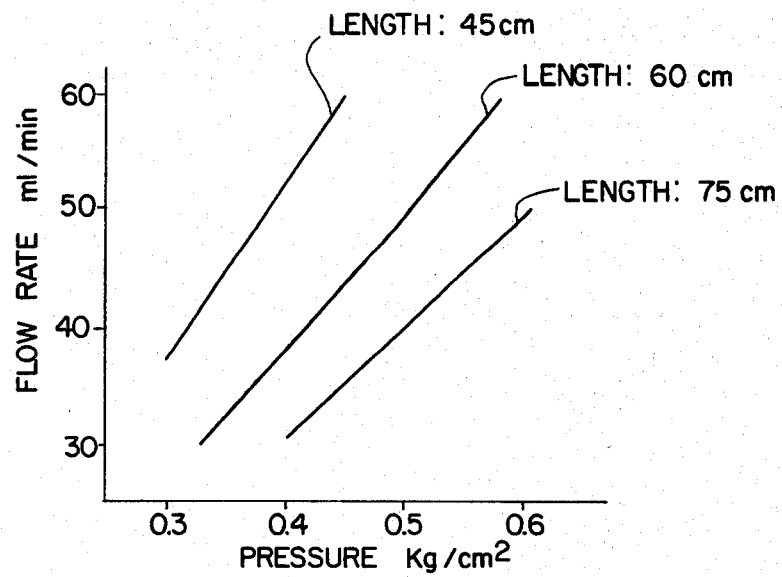
FIG. 2 is a graph showing the relation between the flow rate and the pressure of the carrier gas passing through the porous tubing in the case where three kinds of choking means are employed.

In FIG. 2 there is depicted the relation between the flow rate and the pressure of the carrier gas when several kinds of resistances are used. As the resistance, fixed choking means fabricated of stainless pipes having an inside diameter of 0.3 mm and a length of 45 cm, 60 cm and 75 cm, respectively, are used. When one fixed choking means is used to increase the carrier gas pressure, the flow rate of the carrier gas is also increased. For the reasons it is difficult to achieve, using one kind of fixed choking means, the changing of the pressure with the flow rate kept constant, or the changing of the flow rate with the pressure held constant. Hence in the cases where the pressure of liquid imposed on the porous tubing varies stepwise to a predetermined value, it is preferred to provide several kinds of the fixed choking means and to select one adaptable to the change of the liquid pressure for the supply of the carrier gas.

Actually in the aerobic cultivation of microorganisms the interior of a fermentor is sometimes under slightly increased pressure by the adjustment of an air exhaust line from the fermentor during the course of cultivation, with a view to raising the dissolved oxygen concentration into a culture broth. As such, in a process in which the liquid pressure imposed on the porous tubing varies stepwise, it is preferable from a viewpoint of rapid operation of measurement to set only the pressure to a desired value while maintaining the substantially uniform flow rate of the carrier gas passing through the porous tubing with simple procedures. Meanwhile, in a batch process in which the amount of liquid increases with the lapse of time, the pressure imposed on the porous tubing rises. In such a case a variable choking means is preferred to use which permits continuous changing of choking degree.

When the pressure of liquid to be tested varies greatly with the lapse of time, it is desired to control the pressure difference between the liquid to be tested and the carrier gas to a desired value by the adjustment of the carrier gas passing through the porous tubing manually or automatically in accordance with changes in the liquid pressure detected.

As the variable choking means, there are included a needle valve and a fine flow control valve widely used, the nipping of a flexible passageway with a pinch and the like.

As the fixed choking means, besides pipes having an extremely small inside diameter such as a capillary, there are also included the case where a resistance choking flow is incorporated into a device which is used for removing unnecessary substances other than volatile substances contained in the carrier gas including, for example, steam and the like.

In the event that the supply pressure of the carrier gas varies, pressure compensation and flow rate compensation for a flow meter is necessitated. Moreover, when the supply pressure of the carrier gas varies the sensitivity of the detector's outputs including an influence coming from the change of the flow rate of the carrier gas, so that those have to be compensated.

The compensation of outputs by the carrier gas supply pressure may be carried out predominantly in two manners.

A first method is conducted in which output sensitivity is beforehand determined to each of supply pressures, according to which the measured value is corrected. In this method there are included two ways; one is to compensate the sensitivity manually, the other is to at first convert the carrier gas supply pressure to an electric signal and then automatically compensate the measured signal by a calculating device such as a digital computor and an analog calculator.

A second method is performed by a calibration device of outputs measured by a pressurized container and calibration is carried out at a step of varying the carrier gas pressure. To be more concrete, two sampling means are used. One sampling means is for the measurement of the liquid to be tested. The other is for the calibration in which it is placed in a standard solution containing a known concentration of the substance to be tested. The particulars will be stated later.

In measuring the concentration of a volatile substance in a liquid using the porous tubing, when temperature of the liquid to be tested is lower than that of the carrier gas discharge pipe i.e., atmosphere, the volatile substance and steam passing through the porous tubing are condensed by cooling in the carrier gas discharge pipe. Accordingly if there is the fear of condensation in the passageway of the carrier gas, it is required to heat all the passageway of the carrier gas from the outlet of the porous tubing to the inlet of the detector. In this case, heating of the choking means is also needed to prevent condensation at that portion.

Once a material of the porous tubing, a pore size, properties of a liquid to be tested, the pressure imposed on the porous tubing and the like are determined, it is possible to make the life of the tubing longest by keeping the pressure difference as low as possible by enhancing pressure of the carrier gas passing through the porous tubing. However, when the life of the porous tubing is short compared to continuous measurement time required, inconvenience occurs that the measurement becomes infeasible before the operation terminates. It is therefore required to exchange the porous tubing in use with the other halfway through the continuous measurement to continue the measurement even in such a process as needing much longer operation time exceeding the life of the porous tubing.

The exchange method of the porous tubing includes a method in which the sampling means is removed from the container and exchanged with the other, and another in which a plurality of standby tubings are installed to the sampling means. In this case it is necessary that no leakage of the liquid takes place at the time of exchanging and that the standby porous tubings must be kept new until exchanged. The standby porous tubings, even when not used for the measurement of a volatile substance, are stained on their surfaces while being in contact with the liquid, and are filled with steam and a volatile substance permeating through the minute channels. Moreover, the steam and the substance are condensed in the carrier gas supply and discharge pipes, with a result that their lifetimes are almost finished by the time they are exchanged. In installation of a plurality of porous tubings to one sampling means care must be taken that the porous tubings not in use should not be exposed to the liquid. Instead, a compressed gas had best be jet out into the liquid by connecting a compressed gas supply source to the porous tubings unemployed. Jetting out of the compressed gas prevent stains, adhesive substances and the like from depositing onto the surface of the porous tubings, and consequently the permeation of the liquid into the minute channels is also prohibited, so that those may be maintained as such new. As the compressed gas, there are included nitrogen gas, helium gas, argon gas, air and oxygen, which are equal to the carrier gas. In addition, any other gas may also be employed which gives no adverse influences on the apparatus and the process, and is not reactive with the liquid in the container. In a process such as cultivation of microorganisms extremely disliking invasion of miscellaneous microorganisms, a pure gas or gas obtained by removal of miscellaneous microorganisms by a filter has to be used lest those should be mixed into the compressed gas.

In the sampling means providing a plurality of porous tubings, umemployed tubings may be isolated from the contact with the liquid by a specified shape and construction of the sampling means.

In the cultivation process of microorganisms, it is of importance to suppress the growth of miscellaneous microorganisms other than the desired microorganisms and prevent invasion of those in the system. For the reasons, all of the instruments and meters in contact with the liquid are normally used after being sterilized. The sterilization may be effected by the use of chemicals, heating and the like, but, above all, heating sterilization by the use of steam is the most effective and widely employed for the sterilization treatment of the entire fermentor. Exceedingly effective is to increase pressure of steam fed into the fermentor, pressurize the entire fermentor slightly and enhance the inside temperature. For instance, in the cultivation of yeasts the miscellaneous microorganisms which are a hindrance to the production may substantially be killed by sterilization under heat and pressure where the inside pressure of the fermentor is maintained at 1.0 Kg per $cm^2G$ or more and the inside temperature is heated to 120° C. or more.

Nonetheless the measurement method of a volatile substance in a liquid providing the porous tubing having liquid repellency and continuous minute channels extending through the porous partition tubing wall has several problems in respect of sterilization under heat and pressure.

Firstly, the heat resistance property of the porous tubing is problematical. In this respect a material having sufficient heat resistance at a heat sterilization temperature must be used. The problem is solved by selecting tetrafluoroethylene resin resistant to a high temperature of 200° C. or higher. Secondly, the shape of the porous tubing can not stand increased pressure and thus will be deformed and crushed. Once the circular section of the porous tubing is crushed and deformed at a spot, deformation is apt to occur repeatedly at the same spot and the tubing will not return to the original shape even after removal of pressure. The deformed porous tubing causes narrowed passageway of the carrier gas, thereby resulting unstable causes for measurement including changes in the flow rate and pressure of the carrier gas. Perfectly crushed porous tubing naturally prevents the flowing of the carrier gas to thus make the measurement impossible. Thirdly, under increased pressure, steam is pressed into the carrier gas through continuous minute channels. Fourthly, steam is diffused into the inside of the porous tubing through continuous minute channels since the porous tubing is placed in an ambience filled with steam. The third and fourth problems as aforesaid, to be brief, are to allow a great amount of steam to flow into the carrier gas in the porous tubing. Since a great amount of steam flows into the carrier gas, the steam is condensed to become waterdrops which accumulate in the porous tubing and the carrier gas supply and discharge pipes to thus cause blocking of the carrier gas passageway, what is worse, to invite damage of the detector by entrance of waterdrops into the detector. Even after termination of sterilization under heat and pressure, a problem arises when the measurement starts in a state where a great amount of waterdrops is present in the carrier gas passageway and the continuous minute channels. That is, when a great deal of water is present in the continuous minute channels, the outside of the porous tubing is substantially linked through water to the inside. In this state when the porous tubing is placed in the liquid to be tested, the liquid is linked through waterdrops in the continuous minute channels to the inside of the porous tubing in spite of water repellency thereof, so that the most fundamental function of the porous tubing may not be attained at all which permits passage of a volatile substance alone in the liquid. The waterdrops in the porous tubing or the carrier gas supply and discharge pipes, even in an extremely small amount, dissolve the volatile substance collected in the carrier gas, thus causing changes in the concentration of the substance to greatly lower the accuracy. Moreover the detector is probably damaged, as mentioned above.

The sterilization under heat and pressure of the sampling means positioned to a fermentor is carried out wherein two carrier gas switchover means are located halfway of the carrier gas supply and discharge pipes, a first switchover means at the side of the carrier gas supply pipe is connected to a compressed gas supply source and a second switchover means at the side of the carrier gas discharge pipe is connected to a compressed gas discharge outlet through a choking means. In the case of sterilization, the carrier gas passing through the porous tubing is stopped by the first switchover means, the compressed gas is instead supplied from a compressed gas supply source, then the compressed gas passing through the porous tubing is discharged by the second switchover means from the compressed gas discharge outlet.

The pressure of the compressed gas passing through the porous tubing must be higher than that of the container at the time of sterilization. The flow rate of the compressed gas must be sufficient to smoothly remove steam flowing into the porous tubing. Normally a flow rate of about 1 to 2 liters per min suffices. The compressed gas may be the same kind as the carrier gas. It is further important that the compressed gas per se is not harmful to the microorganisms and contains no harmful substances. Moreover the compressed gas containing no miscellaneous microorganisms or the sterilized gas is preferably used.

The choking means connected to the compressed gas discharge outlet is used, together with the compressed gas supply source, for the adjustment of a flow rate and pressure of the compressed gas.

As stated above, in the case of sterilization the compressed gas supplied from the compressed gas supply source is allowed to flow through carrier gas switchover means, carrier gas supply pipe, porous tubing, carrier gas discharge pipe, carrier gas switchover means and choking means, then removed from the system through carrier gas discharge outlet. On the other hand, the carrier gas supplied from the carrier gas supply source is discontinued by the first switchover means and thus not supplied to the detector.

Dependent upon the kind of a gas detector used, a certain kind of the detector takes a considerably long time after suppy of electric power before it becomes stable. In most cases it is good for stability of the detector that during aging after supply of electric power it should be maintained under the same conditions as those in the measurement. That is specifically applied to, for example, a catalytic combustion type gas detector and metallic oxides solid state gas detector, because the temperature and atmosphere of the detector differ according to passage or non-passage of the carrier gas. Accordingly when these detectors are used, it is preferred, even in sterilization, to supply the carrier gas to the detector, as in the case of measurement. For this purpose it is desirable that a bypass line for supplying the carrier gas directly, without through two carrier gas switchover means, which connects one point between the carrier gas control means and the first carrier gas switchover means to the other point between the second carrier gas switchover means through the porous tubing and the choking means linked to the detector. That is, at the time of sterilization the carrier gas supplied from the carrier gas supply source through the carrier gas control means is introduced to the detector by way of the bypass line and the choking means.

In the meantime, in the case of measurement of a volatile substance, the bypass line is not required because the carrier gas passes through the porous tubing. Hence the switchover means is also necessary in the bypass line for opening or closing at the time of sterization as well as measurement. The bypass line should be preferably determined in length and diameter so that a flow rate and a pressure of the carrier gas be the same when passed through the bypass line at the time of sterilization and when passed through the porous tubing at the time of measurement. By so doing, the carrier gas passes under the same conditions even at the time of sterilization or measurement.

By introducing the carrier gas containing a volatile substance passing through the porous tubing to the detector, a continuous measured value is obtained which corresponds to the concentrations in the liquid. From the continuous measured value obtained, it is necessary to know the actual concentration in the liquid. For the purpose, in the case where a detector which is capable of measuring an absolute value of the volatile substance in the carrier gas is employed, it is possible to obtain the actual concentration by a suitable operation of the detector's output based on gas-liquid equilibrium between the volatile substance and the liquid or a certain relation therebetween. This method, however, has numerous drawbacks that the relation between the concentration of a volatile substance contained in the carrier gas and that of a volatile substance in the liquid has to be determined beforehand, that actual measurement must be performed under the conditions reproduced precisely form the relation determined, and that the detector used is limited.

A second method is the most effective, in which the standard solution of a known concentration is used, as is practiced in calibrating sensitivity or adjusting zero point and the span. In a conventional apparatus for measurement of the concentration of a volatile substance using the porous tubing, however, it is altogether impossible to freely install or remove the portion of the porous tubing positioned in a container filled with a liquid, with the carrier gas supply and discharge pipes connected thereto. Even if this was possible the delicate balance of a flow rate of the carrier gas is varied by movement of the carrier gas supply and discharge pipes, thus to result in rather inaccurate calibration.

Furthermore, even when the output value is calibrated to the liquid of a known concentration by the standard solution while overcoming the foregoing drawbacks, variations in zero point and the span are not calibrated since the sampling means is not moved during the continuous measurement for a long period, with a result that an exceedingly unstable state is unavoidable for the long-term continuous measurement.

One easy calibration method is conducted in which the carrier gas is introduced into a second porous tubing having liquid repellency and continuous minute channels extending through the porous partition tubing wall, positioned in a calibration container filled with a second solution having a known concentration of a gaseous or volatile substance, further having a temperature and a pressure equal to those of the liquid to be tested. The carrier gas is introduced into the second porous tubing through the carrier gas switchover means provided halfway between the carrier gas supply pipe and the carrier gas discharge pipe, then the carrier gas after passage through the second porous tubing is led into the detector by the switchover means, thereby calibrating sensitivity of the apparatus.

As a general rule, the purpose of calibration of zero point and the span is to determine zero point of the apparatus prior to effecting measurement and to adjust or know sensitivity of the apparatus to the liquid to be tested. Moreover in an apparatus in which drift of zero point or variations in the span and sensitivity take place during the long-term continuous measurement, periodical checking and adjustment of those are indispensable. With an apparatus for measurement of the concentration of a gaseous or volatile substance in a liquid using a porous partition tubing having liquid repellency and continuous minute channels extending through the porous partition tubing wall, it is essential not only to calibrate, prior to measurement, zero point and the span, but also to conduct the periodical calibration and adjustment of zero point and the span, because drift of zero point and variations in the span of the detector are liable to take place by delicate variations of atmospheric and operational conditions. Further, the porous tubing deteriorates with the lapse of time.

Between the calibration line introducing the carrier gas into the calibration porous tubing and the measurement line introducing the same into the measurement porous tubing, there should be no difference in flow rate and pressure of the carrier gas. It is therefore necessary to fabricate these two lines under the same conditions including the diameter and the length of pipes. The switchover means has to be selected which is capable of smooth operation without an impact when switched and a variation in pressure. From this respect, an three-way electromagnetic valve, a two-way electromagnetic valve, a multi-way cock and the like may be preferably used.

If a porous tubing, in which the carrier gas does not flow due to the passageway being shifted to another, is placed in a system under rather increased pressure, and thus deformed by liquid pressure or permeated with the liquid through continuous minute channels, it is effective to supply a quasi-gas having the same flow rate and pressure as those of the carrier gas into the porous tubing. That is, as soon as supply of the carrier gas is shifted from one porous tubing to another, a quasi-gas is supplied into the former tubing, then discharged into the atmosphere.

What was mentioned as to the calibration line and the measurement line may be directly applied to the standard solution used for calibration. That is, as the gas-liquid equilibrium is dependent on a variation in temperature, the calibration standard solution and the liquid to be tested should have the same temperature.

Further in the case where a great pressure of the liquid is exerted on the measurement porous tubing and thus the carrier gas has to be supplied under slightly increased pressure, the pressurized carrier gas naturally has to be supplied into the calibration porous tubing. In this case the calibration standard solution should have a pressure equal to that of the liquid to be tested by pressurizing the calibration container.

As apparent from the foregoing, the calibration container is equipped with an agitator, a temperature control device for allowing the standard solution to have the same temperature with the liquids, a pressurizing means for maintaining the standard solution under increased pressure and the like. In practicing calibration of zero point and the span or the span of different concentrations in one calibration container, it should desirably have a construction such that replacement of solutions is feasible. Furthermore, when calibration of the span is practiced periodically and incessantly in the long-term measurement, the system is desired which is capable of measuring the pressure and the temperature of the liquid to be tested, then automatically controlling the pressure and the temperature of the standard solution in the calibration container by the use of a suitable control device.

Hereinafter, an apparatus for practicing a measurement method of the present invention will be described in more detail by referring to the drawings.

Figure 3:
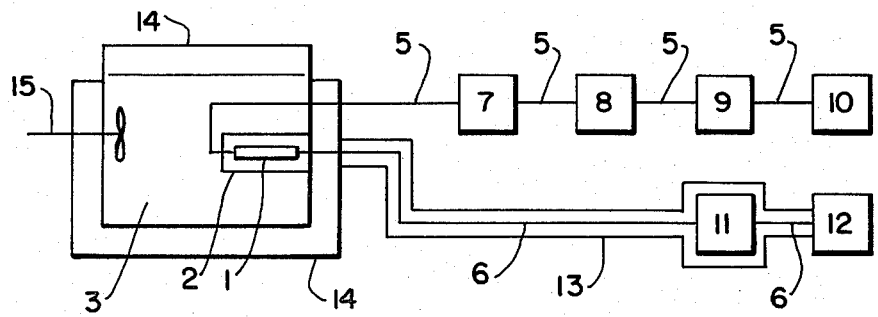
FIG. 3 is a diagram showing the principle of the present invention.

FIG. 3 is a diagram illustrating a basic apparatus of the present invention. The porous tubing (1) is positioned as a sampling means (2) to a container (4) filled with a liquid (3) to be tested. The sampling means (2) is basically comprised of a construction to be positioned to the container (4), a construction of holding a carrier gas supply line (5) and a carrier gas discharge pipe (6), each connected to an opposite end of the porous tubing (1) and a protective cylinder for protecting the porous tubing from the flow of the liquid and producing a smooth movement of the liquid along the porous tubing (1).

One end of the carrier gas supply pipe (5) is connected to a manometer (7), a flow meter (8), a carrier gas control means (9) and a carrier gas supply source (10).

As the carrier gas, an inert gas or air is normally used, above all, nitrogen gas is preferably used. Of course, an optimum carrier gas had best be selected, taking into full consideration the adaptation for a detector used. Moreover, a pure and sterilized gas is preferred against mixing into the liquid. In the case of air, the carrier gas supply source (10) is comprised of a gas bomb and a primary reducing valve, an air compressor and a reducing valve, instrumentation air and a reducing valve or the like.

As the carrier gas control means, a fine flow controller, a fine pressure controller, a needle valve and the like are usable, singly in combination of two or more.

As the carrier gas flow meter and the manometer, those which are widely used are usable, but those which are capable of precisely measuring a minute flow and pressure are desired.

The other end of the porous tubing (1) is connected to a detector (12) through a carrier gas discharge pipe (6) and a choking means (11). In cases where the gaseous or volatile substance is feared to be condensed in the carrier gas, all the passageways from the porous tubing (1) to the detector (12), including the choking means (11), are heated by a heating device (13). The numeral (14) is a liquid temperature control device and (15) is an agitator.

As the material of the carrier gas supply and discharge pipes, a suitable material is selected from metals, synthetic resins, glasses and the like. Needless to say, it is essential to the material of these pipes not to permeate a gas through the wall of the pipes, and those which are liable to adsorb gas molecules on their inner surface or weak in strength are avoided. The carrier gas discharge pipe (6) is heated by the heating device (13), and hence materials which are heat-resistant and heat-transferable are preferably used.

The size of the carrier gas supply and discharge pipes had best be determined, taking into full consideration a flow rate of the carrier gas, the distance between the detector and the porous tubing, carrier gas supply pressure and so on. That is, when an inside diameter of the pipe is great, the passage speed of the carrier gas for a given flow rate becomes slow, thus to increase delay in measurement time, which is contrary to a desire of rapid and accurate measurement. Inversely, in the case of a small inside diameter, the pressure gradient arises to a passing direction of the carrier gas, which gives an inconvenience to an aim of precisely controlling to a given value the pressure of the carrier gas passing through the porous tubing.

A great difference in inside diameters of the porous tubing and the carrier gas supply and dischare pipes causes the carrier gas flow to be turbulent and hence is undesired. The inside diameter of the porous tubing, as a whole, should desirably the same with that of the pipes.

As the heating device, any known heating device may be used which is capable of heating all passageways from the porous tubing to the detector, including the choking means to such a degree that the volatile substance and steam in the carrier gas are not condensed. The pipes and the choking means may be, of cource, heated by separate heating devices. The heating device should have a capacity enough to maintain the carrier gas discharge pipe and the choking means at the temperature of the liquid or higher. Variations in the temperature of the pipes and the choking means place influences on the flow rate and the pressure of the carrier gas, and accordingly it is preferred to adjust the temperature of those to a constant value by the use of a temperature controller.

As the choking means, when the state of the liquid and the pressure at the measuring point thereof are kept nearly constant, a fixed choking means may be used. As the fixed choking means, pipes having an extremely small inside diameter may be exemplified. The pipe can vary a degree of choking i.e., resistance by varying its length.

In the event that the degree of choking is constant, the flow rate and the pressure of the carrier gas vary at the same time, by the operation of the carrier gas control means located at the upstream of the porous tubing. In other words, the flow rate varies according to the pressure. Inversely, so long as such the choking is used, it is impossible to vary the pressure only with the constant flow rate, or the flow rate only under the constant pressure, as shown in FIG. 2.

Figure 4:
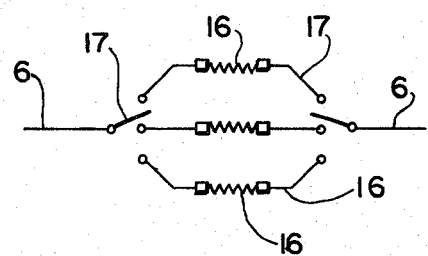
FIG. 4 is diagram illustrating choking means made up of the combination of several pipes having different choking degrees and a switchover means.

In processes increasing the pressure of the liquid with the lapse of time, for example, a fed-batch cultivation process in which the amount of the liquid increases by supplying a substrate with time, or a cultivation process in which a fermentor is pressurized with the lapse of time, the pressure of the carrier gas has to be adjusted according to a variation in the pressure of the liquid. In these cases, as illustrated in FIG. 4. it is convenient to adjust the pressure of the carrier gas by shifting of a plurality of fixed choking means (16) by a switchover means (17), each of fixed choking means being capable of giving the same flow rate to a given pressure. Moreover, the method is also adaptable in which the pressure of the liquid is continuously measured by a manometer, according to which automatic shifting to the optimum choking means is effected by the use of an operating device such as a microcomputor. When a plurality of fixed choking means and the degree of choking are varied by the switchover means, it is desired to employ such a switchover means as not interrupting the flow of the carrier gas. The wide range of adjusting the flow rate and the pressure of the carrier gas may be obtained by the use of a variable choking means. As the variable choking means, a needle valve in use for finely controlling the flow rate may be exemplified. The fixed choking means and the variable choking means are also used, in combination, by being connected in series or in parallel.

As the detector, those which are suitable for the measurement of the concentration of a volatile substance may be commercially obtained and employed, as they are or with an improvement added.

For instance, in the event that the volatile substance contained in the liquid is one kind or substantially regarded as one kind, the carrier gas passing through the porous tubing is introduced into the detector whereby the concentration of the volatile substance can be measured continuously. In the case of ethanol as the volatile substance, a hydrogen ionization detector (FID) provides accurate and stable measurement. When highly accurate measurement is not necessarily required, a cheaper apparatus may be manufactured by the use of detectors including, for example, a catalytic combustion type gas detector, a solid state gas detector and the like. In addition, an infra-red detector, a temperature conductivity gas detector, an electron capture gas detector, a flame photometric gas detector, a magnetic gas detector, a laser gas detector, an absorbance method with a specified wave length and the like may be also employed, depending on the kind of the volatile substance. With the intermittent measurement, a gas detecting tube may be also used.

On the other hand, in cases where a plurality of volatile substances are contained in the liquid or the substances are not substantially regarded as one kind, any separating operation has to be done at the passageway up to the detector, or a detector which is capable of selectively detecting the desired substance alone had best be used. The separating operation is performed with ease by gaschromatography, through this is limited to intermittent measurement.

Figure 5:
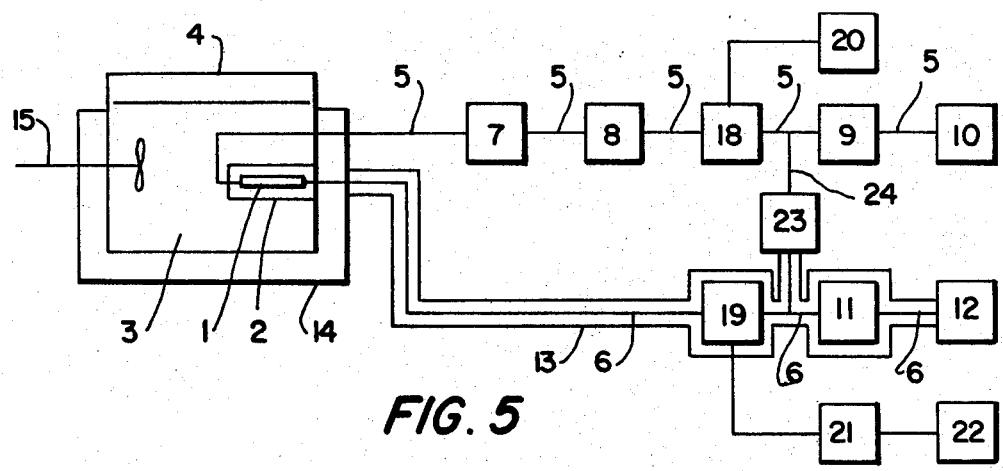
FIG. 5 is a diagram exhibiting the present measurement method and apparatus in which a sampling means can stand heating and pressurizing sterilization by the use of steam.

In FIG. 5, there is depicted an apparatus of the present invention in which the container providing the sampling means including the porous tubing is sterilized under heat and pressure.

On the way of the carrier gas supply pipe (5), a first carrier gas switchover means (18) connected to the compressed gas supply source (20) is provided, and on the way of the carrier gas discharge pipe (6) a second carrier gas switchover means (19) is provided which is connected to the compressed gas choking means (21) and the compressed gas discharge outlet (22). Moreover, a bypass line (24) connected to a bypass line switchover means (23) is provided on the passageway from the carrier gas control means (9) to the carrier gas choking means (11).

In sterilization by steam under heat and pressure of the container (4) filled with the liquid (3), the compressed gas is supplied into the porous tubing (1) by shifting the first carrier gas switchover means (18) and the second carrier gas switchover means (19), then is discharged in the atmosphere through the compressed gas choking means (21) and the compressed gas discharge outlet (22). At the same time, by operation of the bypass line switchover means, (23) the carrier gas is supplied into the detector (12) through the carrier gas control means (9), the bypass line (24) and the carrier gas choking means (11). In this case it is desirable to fabricate the bypass line (24) so that the flow rate and the pressure of the carrier gas passing through the porous tubing (1) may be equal to those passing through the bypass line (24).

In practicing the measurement of the concentration of the volatile substance in the liquid, the carrier gas is supplied into the porous tubing (1) by shifting the first and second carrier gas switchover means (18), (19) and the bypass line switchover means (23), then introduced into the detector (12) through the carrier gas choking means (11). During the course of measurement, no compressed gas flows to a direction of the porous tubing (1) or the carrier gas supply source (10). Needless to say, the carrier gas exiting from the porous tubing (1) is not passed to the compressed gas choking means (21). If there is any possibility that the volatile substance or steam in the liquid is condensed at the time of measurement, all the passageways of the carrier gas from the outlet of the porous tubing (1) to the detector (12), including the second carrier gas switchover means (19), the bypass line switchover means (23), a part of the bypass line (24) and the carrier gas discharge pipe (6), must be heated by the heating device (13) to be, at least, the same temperature of the liquid. As the carrier gas switchover means and the bypass line switchover means, there may be included a two-way valve, a three-way valve, a two-way electromagnetic valve, a three-way electromagnetic valve, a cock, a multi-way cock and an automatic cock. Those can be used singly or in combination of two or more.

The carrier gas switchover means should have a construction permitting no leakage nor accumulation of the liquid inside thereof. If the compressed gas is supplied for sterilization and steam contained in the gas is condensed in the switchover means, such condensed water may invite the blocking of the passageway of the carrier gas or damage of the detector, when the carrier gas is supplied for measurement.

Figure 6:
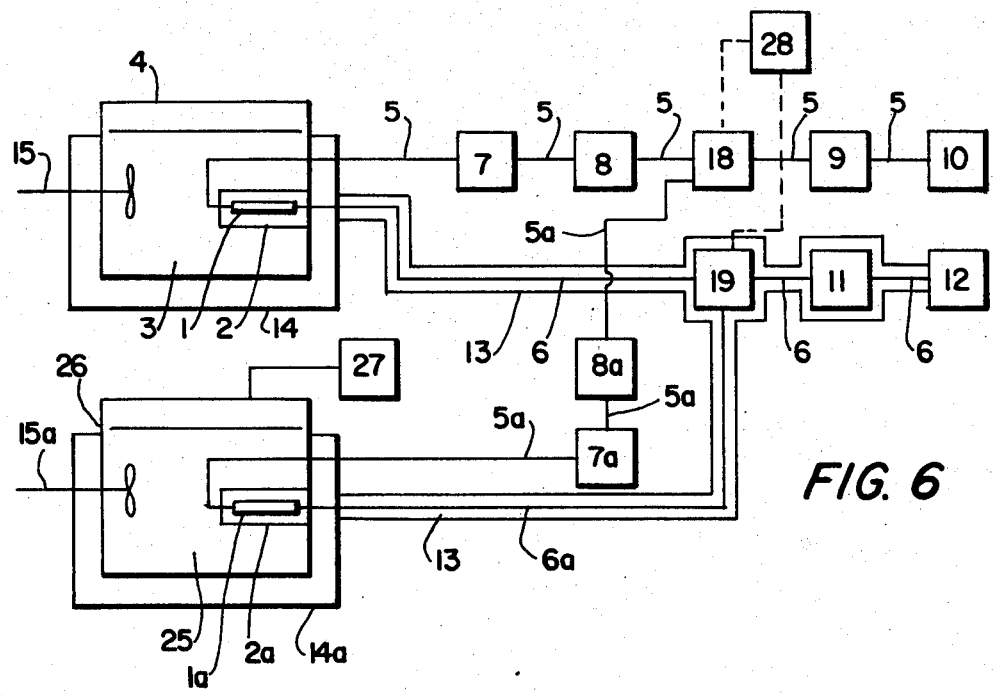
FIG. 6 is a diagram showing the present measurement method and apparatus to which calibration function is added.

In FIG. 6, there is illustrated a calibration apparatus of the present invention in which between the two carrier gas switchover means a second porous tubing is provided in a calibration container filled with a standard solution containing a volatile substance of a known concentration, whereby the output obtained by the measurement apparatus is calibrated at any time to the concentration of the volatile substance in the liquid.

Between the first carrier gas switchover means (18) located on the way of the carrier gas supply pipe (5) and the second carrier gas switchover means (19) located on the way of the carrier gas discharge pipe (6), a second porous tubing (1a) of a sampling means (2a) is provided through another set of carrier gas supply pipe (5a) and carrier gas discharge pipe (6a). The second sampling means (2a) is positioned to a calibration container (26) filled with a standard solution (25) containing the volatile substance of a known concentration. The calibration container (26) is equipped with an agitator (15a), a temperature control device (14a) and a pressure control device (27). No change in the carrier gas in respect of the flow rate and the pressure is permissible between the calibration line supplying the carrier gas into the calibration (second) porous tubing (1a), and the measurement line supplying the same into the measurement porous tubing (1). For this purpose, both lines should be fabricated under the same conditions including the diameter and the length of the supply or discharge pipe. Although the same shape is not required as to the sampling means, the porous tubing per se should be from the same manufacture lot as well as the same in length, diameter, pore size and porosity. That is because accurate calibration can not be expected since the quanitity of the volatile substance passing through the porous tubing varies, if the specification differs from each other even with a slightest range. With the use of the porous tubings different from each other, the difference in sensitivity of the two is calibrated and compensation is indispensable.

As the carrier gas switchover means, those which are capable of switching as smoothly as possible while avoiding an impact at the time of switching and a change in pressure of the carrier gas may be effectively used. The carrier gas switchover should have a construction permitting no accumulation of the liquid inside thereof. In this respect, a two-way valve, a three-way valve, a two-way electromagnetic valve, three-way electromagnetic valve, a multi-way cock and the like may be used, singly or in combination of two or more.

The passageways of the carrier gas exiting from the porous tubing to the detector including the carrier gas discharge pipes (6, 6a), the carrier gas switchover means (19) and the choking means (11) must be heated by the heating device (13) to become a certain temperature not lower than the temperature of the liquid. An electric heater, a steam tracing, a heated water tracing and the like may be served as the heating device.

The standard solution for calibration should not only have a known concentration of the volatile substance to be measured, but have the other substances equal to those of the liquid to be tested, because gas-liquid equilibrium differs dependent on the composition of the substances.

The gas-liquid equilibrium depends on a change in the temperature of the liquid, so that the standard solution for calibration should have a temperature equal to that of the liquid to be tested. When the temperatures are different from each other, output values must be compensated to the temperature of the liquid according to the relation obtained beforehand. The temperature compensating device is preferred which automatically compensates the output values. Moreover, the carrier gas is supplied under slightly increased pressure into the measurement porous tubing, and accordingly into the calibration porous tubing the pressurized carrier gas is also supplied. Hence the standard solution for calibration is allowed to have almost the same liquid pressure with the liquid to be tested by exerting the pressure on the calibration container. The standard solution for calibration should not necessarily have the pressure perfectly equal to that of the liquid to be tested, but be under increased pressure enough to prevent the carrier gas from jetting out into the liquid through continuous minute channels of the calibration porous tubing. Furthermore, flow of the liquid has a considerable influence on the sensitivity of measurement. In a practical and industrial process, the liquid to be tested is usually attended by flow, more or less, and as such, the standard solution has to be afforded flow similarly by operation of an agitator (15a).

In practicing the calibration of zero point and the span or the span of different concentrations in one calibration container, it should desirably have a construction such that replacement of solutions is rapidly possible. Moreover when the calibration of the span is conducted periodically and incessantly in the long-term measurement, the system is desirable which is capable of measuring the pressure and the temperature of the liquid to be tested, and automatically controlling the pressure and the temperature of the standard solution in the calibration container by the use of a suitable control device.

Furthermore, it is possible to know at any time, the actual concentration of the volatile substance by automatically shifting two carrier gas switchover means at intervals by means of the switchover controller (28) to obtain the value of the volatile substance of a known concentration through the calibration porous tubing immersed in the calibration solution, and, at the same time, to obtain the value of the volatile substance through the porous tubing immersed in the liquid to be tested, then comparatively calculating the both values to thereby hourly indicating the concentration of the volatile substance in the liquid with an industrial value. The automatic shifting of the carrier gas switchover means and the comparative calculation of the measured values by means of a switchover controller (28) may be achieved with ease by various computors such as a microcomputor, a minicomputor, and a personal computor, a sequencer, a calculator, a direct digital controller and the like. Of course, the carrier gas switchover means which can be operated by an electric signal and so on from the outside is necessitated.

Figure 7:
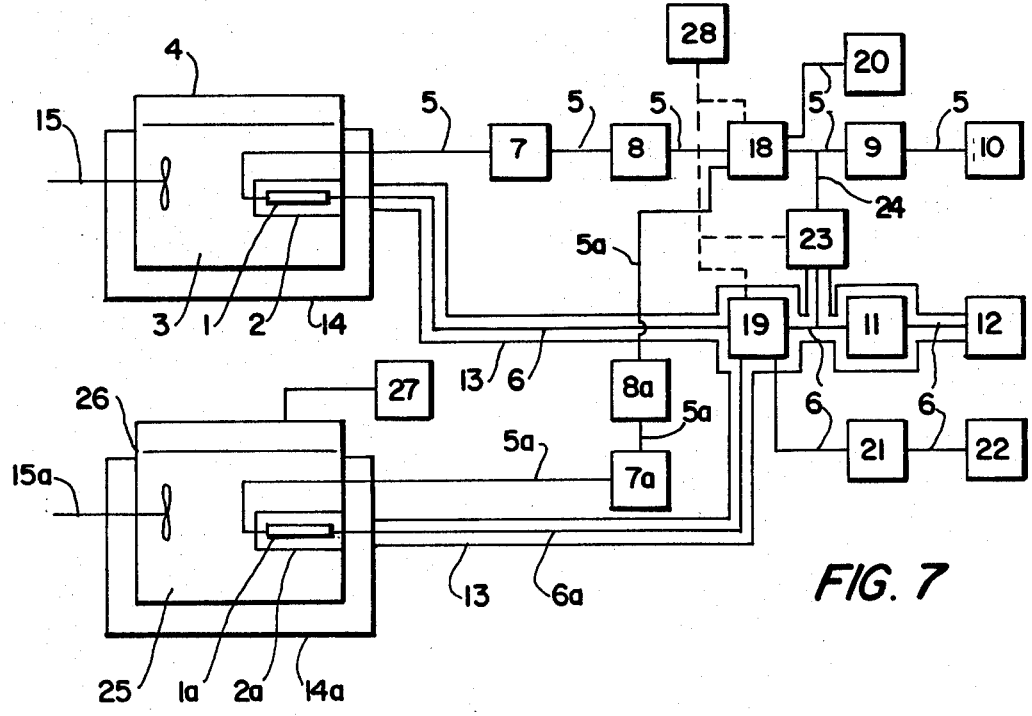
FIG. 7 is a diagram illustrating the present measurement method and apparatus in which a sampling means that can stand heating and pressurizing sterilization by steam is used, besides calibration function.
Figure 9A:
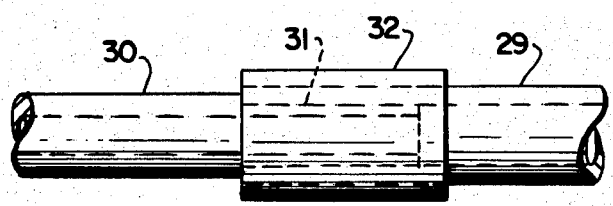
FIG. 9 is a diagram illustrating a porous tubing whose connected portion to carrier gas pipes is reinforced.
Figure 9B:
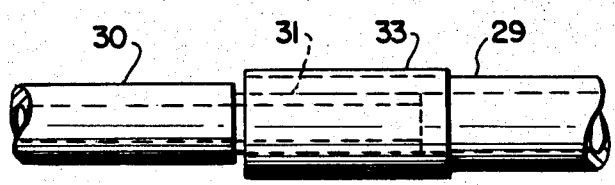
Figure 9C:
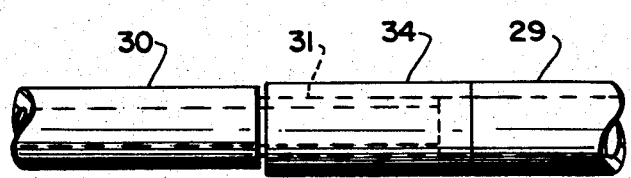
Figure 9D:
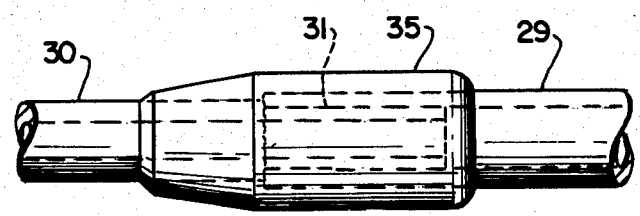

On the other hand, it is desired to supply a quasi-carrier gas into the porous tubing not in use for measurement or calibration. Especially when the pressure of the liquid is high, the porous tubing is possibly deformed, and thus the quasi-carrier gas had best be passed through the tubing. It is effectively accomplished by such a construction that to the both ends of the carrier gas switchover means, a quasi-carrier gas supply and discharge pipes are connected, respectively, and being smoothly replaced with the carrier gas supply for measurement. It is feasible to provide a measurement apparatus of the concentration of a volatile substance in a liquid which has a construction of both sterilization function and calibration function. Referring now to FIG. 7, on the way of the carrier gas supply pipe (5) a first carrier gas swithover means (18) is provided and at the upstream the carrier gas supply line is connected, comprising the carrier gas control means (9) and the carrier gas supply source (10), while the compressed gas supply line connected to the compressed gas supply source (20) is connected in parallel with the carrier gas supply line. At the downstream of the first carrier gas switchover means (18), the two lines are connected in parallel with each other; one is connected through the carrier gas supply pipe (5) to the measurement porous tubing (1) of a first sampling means (2) located at the measurement container (4) filled with the liquid to be tested, the other is connected through the carrier gas supply pipe (5a) to the calibration porous tubing (1a) of a second sampling means (2a) located at the calibration container (26) filled with the standard solution (25) containing a volatile substance of a known concentration.

To each of the other ends of the porous tubings (1), (1a), a second carrier gas switchover means (19) is connected in parallel through the carrier gas discharge pipes (6), (6a). To the other end, i.e., at the downstream, two lines are connected in parallel; one being connected to the detector (12) through the choking means (11), and the other being connected to the compressed gas discharge outlet (22) through the compressed gas choking means (21). Moreover the carrier gas can be directly supplied from the carrier gas control means (9) to the carrier gas choking means (11) through the bypass line (24) on which the switchover means (23) is provided, without via the carrier gas switchover means (18),(19). Likewise, by the operation of the second carrier gas switchover means (19), the gas passed through the porous tubing (1) or (1a) is introduced through the carrier gas choking means (11) into the detector (12), otherwise through the compressed gas choking means (21) to the compressed gas discharge outlet (22). In the practical usage of the apparatus, these three switchover means i.e., first and second carrier gas switchover means (18),(19) and the bypass line switchover means (23) should be desirably operable sequentially. For instance, the carrier gas supplied must be passed through the porous tubing and finally led to the detector, whereas the compressed gas must be discharged from the compressed gas discharge outlet in the long run. These two gasas should not be mixed. Further while the compressed gas being supplied, the carrier gas must be introduced to the detector through the bypass line, on the other hand, while the carrier gas being supplied into the porous tubing, flowing of the carrier gas through the bypass line is not desired. The carrier gas supply pipes should desirably have flow meters (8) and manometers (7) and the calibration container (26) should desirably be equipped with the temperature control device (14a) of the standard solution (25), the agitator (15a) and the pressure control device (27). When the volatile substance and steam in the carrier gas may condense, the passageways of the carrier gas from the outlet of the porous tubings, (1), (1a) to the detector (12) must be heated to keep a temperature not lower than the temperature of the liquid, including the second carrier gas switchover means (19), the carrier gas choking means (11) and carrier gas discharge pipes (6),(6a). Furthermore, the calibration container should preferably be provided with the temperature control device for control of the temperature of the standard solution equal to that of the liquid, the pressure control device for control of the pressure imposed on the calibration porous tubing equal to that imposed on the measurement porous tubing by detecting the latter pressure, the automatically shifting means of three switchover means, the calculating device of the concentration of the volatile substance in the liquid from the outputs of the known concentration thereof in the standard solution, the temperature compensation calculating means for calculating to compensate the outputs to those at a given temperature based on the relation between the temperature of the liquid and the concentration of the volatile substance permeating into the carrier gas, and so on. It should, in addition, have the means for supply and discharge of the quasi-carrier gas to and from the porous tubing. It is also possible to allow the compressed gas supply and discharge pipes to have the foregoing function.

Using the apparatus which is provided with the measurement porous tubing and the calibration porous tubing, the measurement of the concentration of volatile substances in two different liquids may be also effected by using the calibration porous tubing as the measurement one.

Figure 8:
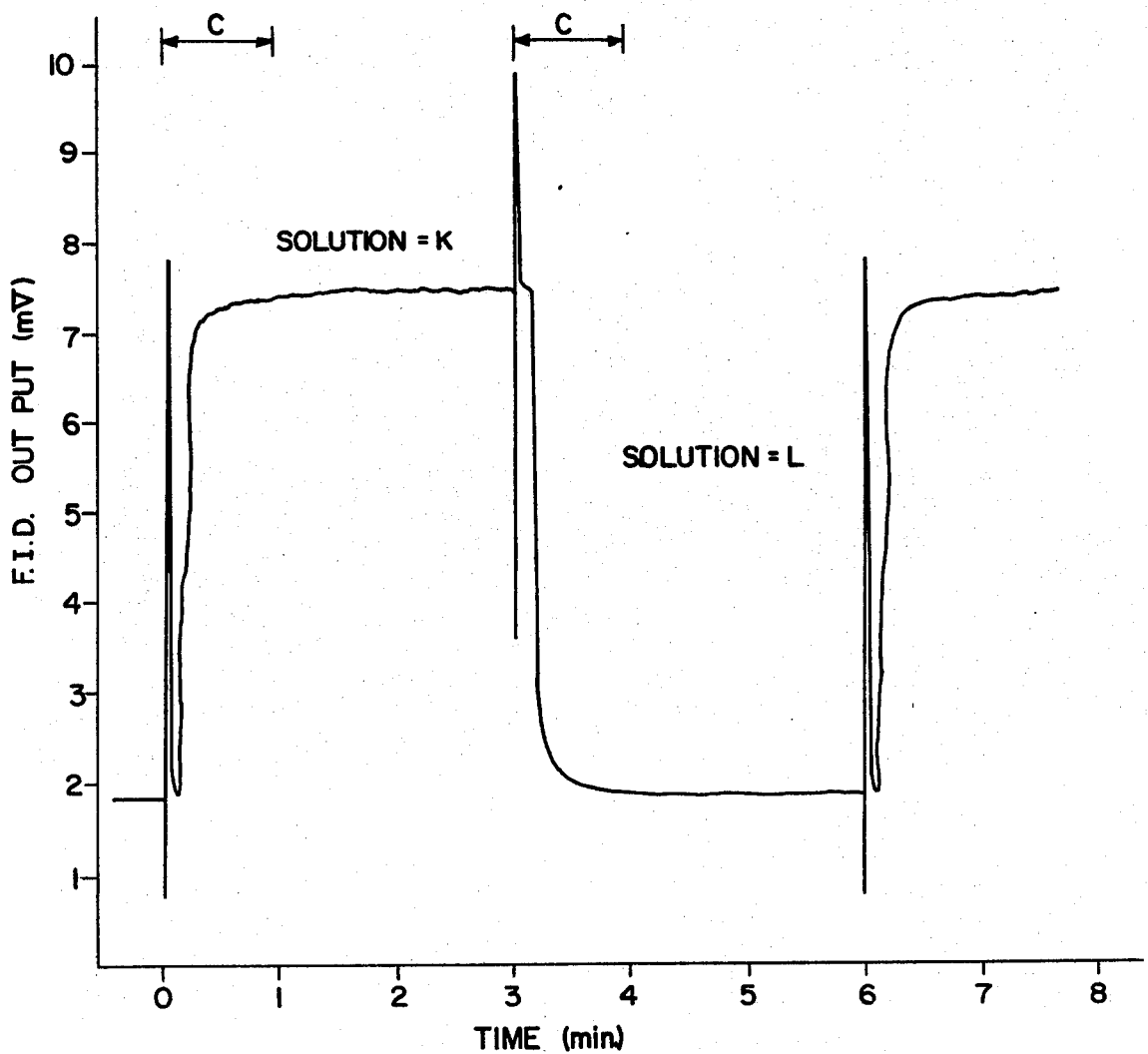
FIG. 8 is a graph showing an output signal measured by changing the liquids to be tested in Example 5.

As a rule, in conducting accurate measurement, a hydrogen flame ionization detector may be preferably served as the detector, as stated earlier. However, most of accurate detectors including the hydrogen flame ionization detector are expensive. On the other hand, in measuring the volatile substance in the liquid there are included in objective processes a case where the concentration of the volatile substance in the liquid varies slowly and a case where it does not matter if the measured signal is discontinuous, since monitoring of the concentration is only necessary. When such processes as aforesaid are arranged in series, installation of one apparatus including one detector for every process becomes costly and thus uneconomical. Although depending upon the minimum intervals of time during which the measurement has to be accomplished in a process, it is theoretically possible to achieve measurement with one detector in a plurality of processes, provided that a plurality of sampling means with porous tubings, equal in number to the processes, are prepared. One of the plural porous tubings may, of course, be placed in the standard solution containing a volatile substance of a known concentration to thus practice calibration. Of course, the larger the number of sampling means linked together, the longer the time taken for the measurement of the objective liquid is. When many sampling means are used, the operation of the carrier gas switchover means should desirably be automated by controllers. In the case of the carrier gas being shifted from one liquid to another, turbulance of the carrier gas unavoidably takes place to thereby cause a disorder in the output as shown by the part of C in FIG. 8. For that reason the time at which a disorder of the output occurs should be observed beforhand, then the disordered output be disregarded. Disregard of the disordered output may be also accomplished with ease by the use of a computor, a digital controller and so on.

The porous tubing used in the present invention should have strong liquid repellency and continuous minute channels extending through the porous partition tubing wall. As the material of the porous tubing, there are included a variety of synthetic resins such as tetrafluoroethylene resin, ethylene halide resin, vinylidene halide resin, polypropylene resin, polyester resin, polyvinyl chloride resin and vinyl halide resin. Above all, tetrafluoroethylene resin is the most preferable. The porous tubing may be made by imparting liquid repellency to porous tubings with no such property.

The porous tubing used in the present invention may be circular, elliptical, quadrilateral or of any cross sectional shape, provided that it is a suitably shaped hollow body satisfying the conditions required for use in respect of surface area and strength. The porous tubing may also be employed having in part of the periphery thereof a liquid repellent porous partition sheet having continuous minute channels extending therethrough.

In the case of the porous tubing of tetrafluoroethylene resin which is found to be most preferable to use, it should suitably, in particular, have an average pore size of about 0.1 to about 1.0 μm and a porosity of about 20 to about 80%, and most suitably in respect of permeability, durability and mechanical strength, have an average pore size of about 0.5 μm, a porosity of about 50 to about 60%, an outside diameter of about 3 to about 4 mm, an inside diameter of about 2 to about 3 mm and a thickness of about 0.5 mm.

The porous tubing, both ends of which are connected to the carrier gas supply pipe and the carrier gas discharge pipe, respectively, to forms the sampling means.

Meanwhile there are brought about numerous problems especially in respect of connection of the porous tubing and those supply and discharge pipes, because the conditions for measurement not only include the cases including cultivation process of microorganisms where violent flow of the liquid takes place on account of aeration and/or mechanical agitation, but the porous tubing per se is of a specific structure. For instance, the diameter of each pipe should desirably be equal to that of the porous tubing and so when intended to be realized, the outside diameter is larger than the inside diameter of the porous tubing. As such, the inside diameter of the porous tubing, when connected by covering to the pipe, is necessarily enlarged to thereby result in the decrease in thickness of the tubing and the increase in pore size. As a result, in the vicinity of the connected portion the suitable balance among the pore size, properties of the liquid and the pressure is destroyed to thus permit the ingress of the liquid through the minute channels of the porous partition tubing wall. What is worse, the connected portion is secured tightly over the porous tubing with a wire, a hose band or the like and thus the minute channels at that portion are crushed or the tubing material is weakened. Moreover due to violent flow of the liquid the porous tubing is subjected to chord-like oscillations between both connected portions so that considerably great pressure is exerted on the connected portions. In addition, since the inside surface of the porous tubing is choffed, at the connected portions, repeatedly with the harsh edge of the pipe, thus leading to deterioration in the material, occurrence of cracks, increase in the pore size and decrease in the thickness of the tubing. These cause ingress of the liquid into the porous tubing or destruction of the tubing.

In solving these problems, good results are obtained by the use of the porous tubing devoid of continuous minute channels, having a smaller pore size and/or a lower porosity at the connected portions, otherwise by the use of the porous tubing of which connected portions are reinforced. The porous tubing having a half or below of the porosity of about 50 to about 60% and the pore size of about 0.4 to 0.5 μm, which are satisfactory in respect of strength and performance, i.e., the porosity of about 30% or below or the pore size of about 0.2 μm or below at the connected portion gives satisfactory results. The porous tubing with no pore size at the portion is, of course, most suitable.

FIG. 9 shows examples of reinforced connected portion of the porous tubing and the carrier gas supply or discharge pipe.

In FIG. 9-(A), there is illustrated an example wherein the connected portion is covered with a tube (32) to reinforce it in a doublewalled tubular construction. FIG. 9-(B) shows that the connected portion is reinforced by coating (33) with a synthetic resin. FIG. 9-(C) depicts that the reinforcement is performed by covering the connected portion with a tape or film (34). FIG. 9-(D) illustrates that the connected portion is reinforced by being molded with a synthetic resin (35). In FIG. 9, the numeral (29) is the porous tubing, (30) is the carrier gas supply or discharge pipe and (31) is a connecting edge which is part of the foregoing pipe. The material of the double-walled tubing, the tubing to be covered, the film or tape may include synthetic resins, synthetic rubbers and the like, among which materials of fluorocarbon series and silicone series resins are especially preferable for use.

The material of the coating or molding may include synthetic rubbers, synthetic resins and the like, among which silicone series rubbers as those having resiliency and epoxy series resins as those devoid of it are preferable for use.

When the surface of the porous tubing is subjected to the treatment such as bonding and coating, such treatment is not so easy because of its strong liquid repellency. Accordingly the portion bonded or coated has to be subjected to surface treatment.

As the method of surface treatment of the porous tetrafluoroethylene, any known methods such as a metallic sodium-ammonium method, a metallic sodium-naphthalene mixing tetrahydrofuran method and the like may be effectively used. Since the surface-treated portion is liable to get wet with the liquid, the portion should by no means be in contact with the liquid under measurement. More effective results are provided by reinforcing a length of about several mm toward the measuring portion of the porous tubing from the edge of the pipe inserted into the porous tubing.

As the method or structure of connecting the porous tubing to the carrier gas supply or discharge pipe, various methods and structures may be effectively employed, including the structure in which the carrier gas pipe is inserted into the porous tubing and the overlapped portion being secured tightly with a wire, a hose band, a heat-contractible tubing, a combined use of a heat-contractible tubing and a silicone series sealant, a ring and a box nut, or the like.

Figure 10A:
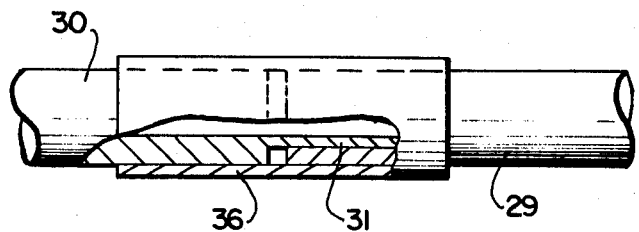
FIG. 10 is a diagram showing a method for connecting a porous tubing to carrier gas pipes and the construction of the connected portion.
Figure 10B:
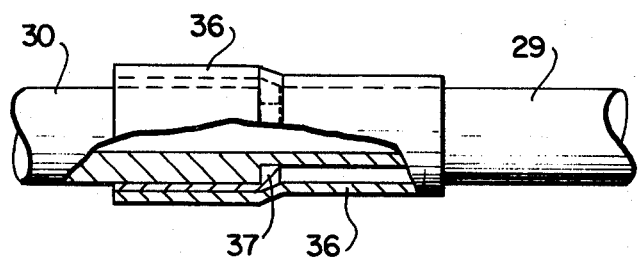
Figure 10C:
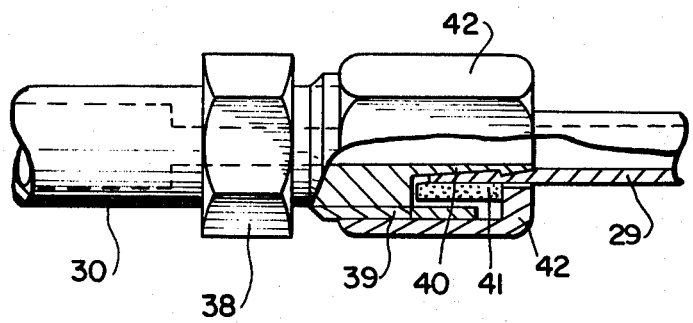

In FIG. 10-(A), there is depicted a structure wherein the connecting edge (31) of the carrier gas pipe (30) is inserted into the one end of the porous tubing (29), the overlapped portion is secured tightly by being covered with a heat-contractible tubing (36). As the heat-contractible tubings, those which contract at about 100° C., and have heat resistance up to about 200° C. and a contraction ratio to a direction of diameter of 20% or more are preferred for use. As the material thereof, a fluorocarbon series resin is preferable but other materials are, of course, usable. In covering the porous tubing with the heat-contractible tubing, only the overlapping portion of the pipe and the tubing should be covered and tightened, if not, the porous tubing is undesirably deformed.

FIG. 10-(B) illustrates a case that between the heat-contractible tubing (36) and the porous tubing (29), and between the porous tubing (29) and the carrier gas pipe (30), a silicone series sealant (37) is charged. Instead of the slicone series sealant any known bonding or sealing material is usable. The silicone series sealants widely in use as bonding or sealing materials for electric and general uses are usable.

FIG. 10-(C) illustrates a structure in which the connecting edge (40) or the carrier gas pipe (30) having the nut (38) and the screw (39) is inserted into the porous tubing (29), the ring (41) is put over the tubing (29), then the box nut (42) is secured to the screw (39). The ring (41) may preferably be resilient tubes or rings made of silicone resins, silicone rubbers and the like, but other materials such as metals, synthetic resins and the like which is capable of tightening without damaging the porous tubing may be also employed. The connecting edge (40) is not necessarily integrated with the screw (39). The porous tubing, into the end of which the connecting edge (40) is inserted, may be also usable. In the foregoing structure the ring (41) is pushed to a longitudinal direction and deformed to thus press-seal the space inside the box nut (42), thereby the porous tubing (29) is pressed against the connecting edge (40) to provide perfect seal.

The sampling means should have a structure such that it is installed to the container filled with the liquid to be measured as well as it holds the porous tubing and the carrier gas pipes. It should preferably have, further, the protective cylinder which protects the porous tubing from vigorous flow of the liquid, at the same time, allow the liquid to flow along the porous tubing, the temperature detector for compensating the output of the concentration according to variations in temperature of the liquid, and the temperature detector protective cylinder into which the temperature detector is inserted.

Since gas-liquid equilibrium varies according to changes in temperature of the liquid, when temperature of the liquid varies by 1° C., the output of the concentration of the volatile substance varies by several percent, with the concentration of the volatile substance in the liquid being constant. Accordingly it is normal that measurement of the temperature of the liquid is made concurrently with the measurement of the concentration of the volatile substance. It becomes complex and needs two installation places to install to the container the temperature detector and the sampling means separately, so that the temperature detector should be incorporated into the sampling means.

Figure 11:
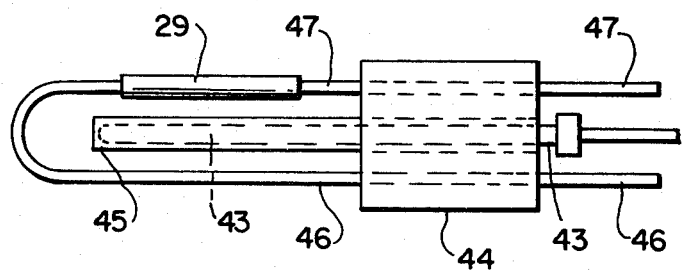
FIG. 11 is a diagram exhibiting a sampling means to which a temperature detector is installed.
Figure 14A:
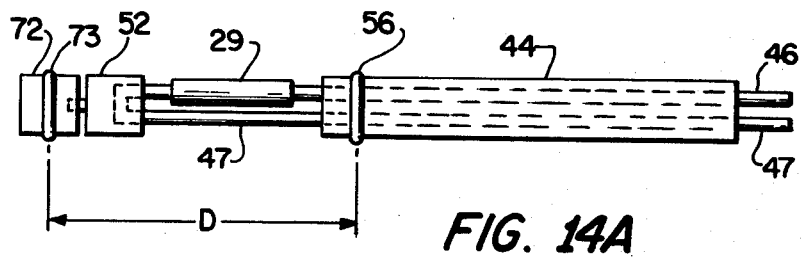
FIG. 14 depicts a sampling means with a plug wherein (A) is a sampler body, (B) is a protective cylinder, (C) illustrates the installation of the sampling means to the wall of the container and (D) shows the practicing of inspection of a porous tubing with the sampling means intalled to the wall.
Figure 14B:
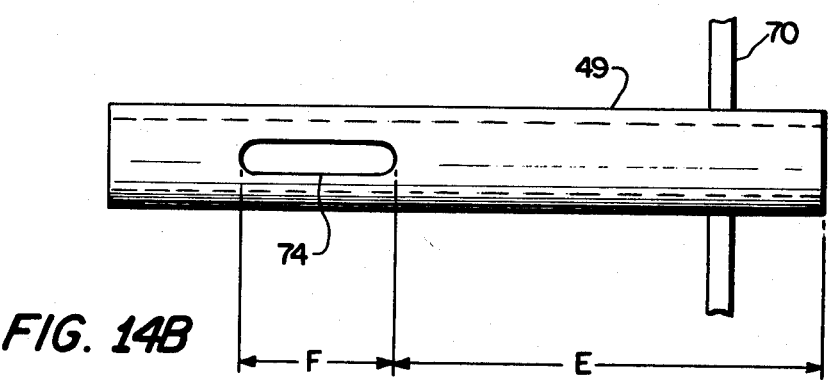
Figure 14C:
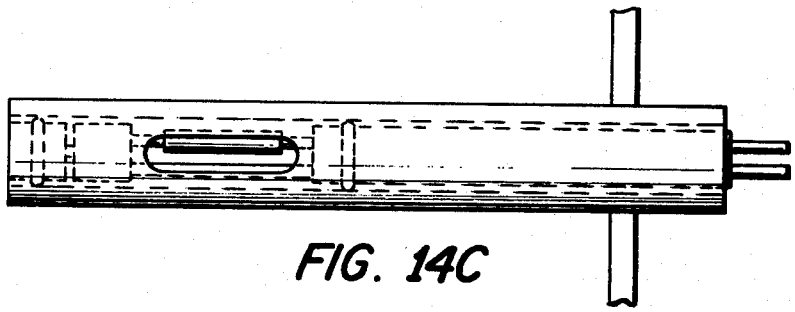
Figure 14D:
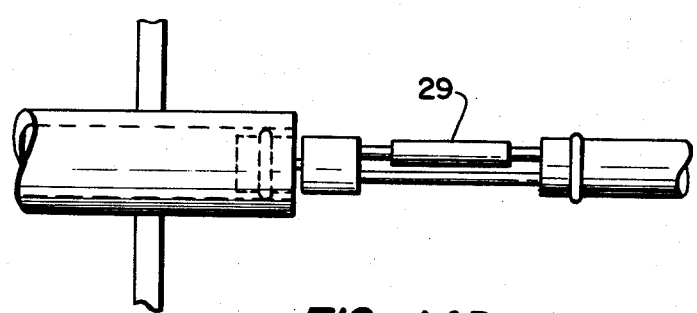

In FIG. 11, there is illustrated a sampling means in which a temperature detector is incorporated. It is rather favorable, in most cases, in respect of replacement and inspection of the temperature detector to install it in the protective cylinder provided to the sampling means than to allow it to come in direct contact with the liquid. In the figure, the temperature detector (43) is inserted into the temperature detector protective cylinder (45) which is positioned to the main holder (44) of the sampling means. The numeral (46) is the carrier gas supply pipe and (47) is the carrier gas discharge pipe.

The protective cylinder plays the role of protecting the porous tubing from flow of the liquid and regulating flow of the liquid around the porous tubing.

The protective cylinder possesses at least one suitable opening permitting contact of the porous tubing with the liquid. When flow of the liquid is strong in a vertical direction to the tubing, great pressure is imposed on the connected portions of the both ends of the tubing. Hence flow of the liquid along the longitudinal direction of the tubing is desirable. For that purpose the protective cylinder should desirably have the openings at the portion over the vicinity of the connected portions of the porous tubing, and at the other portion over the porous tubing per se, should desirably have less or smaller openings or be devoid thereof whatsoever. Moreover in order to remove air bubbles in the liquid remaining in the protective cylinder, up-and-down movement of the liquid had best be utilized. A process is effective wherein the sampling means is installed obliquely to the container to produce the vertical difference in position between the openings provided at the both ends of the protective cylinder. Another is also effective wherein one opening is provided at the uppermost portion of the protective cylinder, while the other opening at the lowermost portion thereof. The purpose may also be achieved by considering a direction of installing the sampling means.

In FIG. 12, the sampling means is installed obliquely to the container wall (48) to produce the vertical difference between the upper opening (50) and the lower opening (51) provided to the protective cylinder (49), so that the liquid and air bubbles contained therein may flow smoothly along the porous tubing. The numeral

(29) is the porous tubing, (52) is the head holder, (46) and (47) are the carrier gas pipes, (53) and (54) are openings of the protective cylinder, and (55) is the sampler installation inlet.

FIG. 13 indicates an example that the protective cylinder comprises a double-cylinder structure composed of an inner and an outer cylinder and both cylinders are variable axially in position relative to each other.

In FIG. 13-(A) shows the sampler body holding the porous tubing (29) and the carrier gas pipes (46), (47). FIG. 13-(B) is an inner cylinder, FIG. 13-(C) is an outer cylinder. In FIG. 13-(D) illustrates that the foregoing sampling means, inner cylinder and outer cylinder are fabricated to form the structure under measurement, then installed to the container filled with the liquid to be tested.

In the figure, by moving axially one of inner and outer cylinder, the opened area formed by changing the overlapping area of the openings (59), (65) and (60), (66), corresponding to each other is variable. The cylinders should be in a cylindrical shape for axial movement. The space between the cylinders (49), (64), suitable sealing means (61), (62) and (56) such as an 0-ring are interposed to provide perfect seal. The numeral (29) is the porous tubing, (46) and (47) are carrier gas pipes, (57) is the main holder stopper, (67) is the outer cylinder stopper, (70) is the container wall, (71) is the sampler installation inlet, (68) is the sealing means between the outer cylinder (64) and the sampler installation inlet (71), (69) is the device for securing the inner cylinder (49) to the head holder (52). Furthermore it is possible to afford various and high degree functions to the present sampling means.

As stated above, continuous measurable time of the method and apparatus of the present invention is dependent on the lifetime of the porous tubing employed. On the surface of the porous tubing, during the long-term measurement, stains and the like deposit. Deposition of the stains and the like causes destruction of the balance among liquid repellency and pore size of the porous tubing, and properties and the pressure of the liquid to thus permit ingress of the liquid through the continuous minute channels, thereby measurement being hindered. It is therefore desired that inspection and replacement of the porous tubing is feasible during the course of measurement. In such cases it is necessary to effect inspection, replacement and washing, with the sampling means installed to the container filled with the liquid under measurement, while minimizing the amount of the liquid flowing out from the container.

In FIG. 14 there is illustrated a sampling means which enables inspection, replacement, washing and the like of the porous tubing with the minimum leakage of the liquid, without removing the sampling means from the container.

FIG. 14-(A) depicts the sampler body integrated with the plug (72) having the sealing means (73) of O-ring. The sampler body comprises the main holder (44) having the sealing means (56) and holding, as one body, the carrier gas supply pipe (47), the carrier gas discharge pipe (46) and the porous tubing (29), and the head holder (52). The head holder (52) is connected by bolting to the plug (73) axially and releasably.

FIG. 14-(B) is the protective cylinder (49) installed to the container wall (70) filled with the liquid. The protective cylinder (49) should have smooth inner or outer surface, the inside diameter which accomodates the sampler body axially and releasably, and provide perfect seal by the sealing means (73), (56) provided to the sampler body, and an open end at one end for accommodation of the sampler body. The protective cylinder should desirably have a length sufficient to accommodate the sampler body and the plug. In the case of using the protective cylinder whose both ends are open, it should be long enough to accommodate the sealing means (73) of the plug (72), when the sampler body is normally accommodated therein. The protective cylinder is equipped with an opening (74) permitting entrance and exit of the liquid. It is required that the entirely cylindrical portion E from the end of the sampler body insertion up to the opening (74), as shown in FIG. 14-(B), should be longer than the distance D between the two sealing means (73), (56), as shown in FIG. 14-(A). Moreover the length F of the opening (74) provided on the protective cylinder should be shorter than the foregoing distance D.

FIG. 14-(C) indicates that the sampler body shown in FIG. 14-(A) is accommodated in the protective cylinder (49) given in FIG. 14-(B) to be ready for measurement. The opening should be positioned between the both sealing means (73), (56), to thus provide complete seal. In practicing replacement, washing or inspection of the tubing (29) after the sampling means was installed to the container filled with the liquid, the sampler body is slidably removed to the position as indicated in FIG. 14-(D), the purposes thus being attained. In this case the leakage of the liquid is only equal to the amount of the liquid present in the protective cylinder partitioned by the both sealing means (73), (56).

Figure 15E:
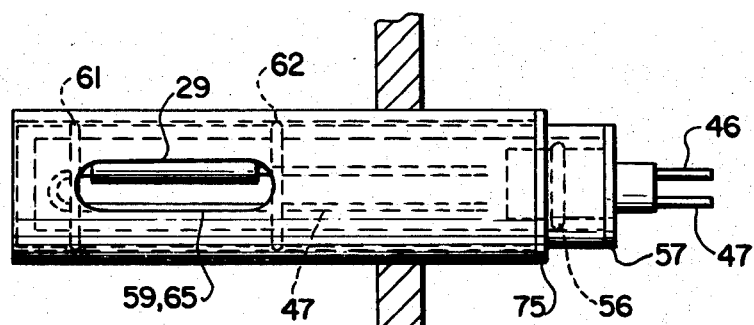
FIG. 15 is a diagram illustrating a double-cylinder sampling means which can be replaced and inspected with ease, wherein (A) is a sampler body, (B) is an inner cylinder, (C) or (D) indicates an outer cylinder, (E) depicts the installation of the sampling means to the wall of the container, and (F) illustrates the performance of inspection of a porous tubing with the sampling means installed to the wall.
Figure 15F:
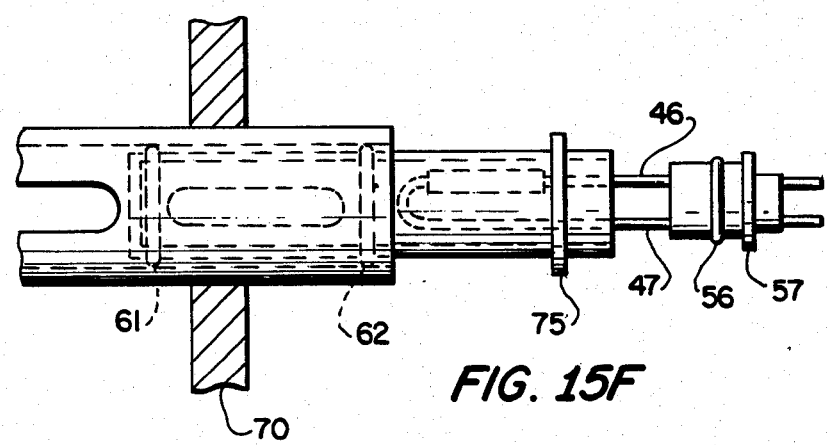

FIG. 15 depicts a sampling means of a double-cylinder construction which is capable of replacement, inspection or washing of the porous tubing while minimizing the amount of leaking liquid, without removing the sampling means from the container filled with the liquid.

FIG. 15-(A) illustrates a sampler body having the sealing means (56) such as an O-ring on the main holder (44). The numeral (47) is the carrier gas supply pipe, (46) is the carrier gas discharge pipe and (29) is the porous tubing.

FIG. 15-(B) is an inner cylinder accommodating the sampler body, the one end being open and the other end being closed.

The entirely cylindrical portions at the respective sides of the opening (59) are provided with sealing means (61), (62) such as an O-ring. The inside and outside surfaces should desirably be smooth and have the inside diameter which holds releasably the sampler body given in FIG. 15-(A) and achieves perfect seal by the sealing means.

Depicted in FIG. 15-(C) is an outer cylinder in which the inner cylinder is accommodated. The outer cylinder, providing the sampler body, is installed to the container wall (70). It should be open at one end to accommodate therein the inner cylinder and have a smooth inside surface and an inside diameter, sufficient to achieve perfect seal by means of sealing means (61), (62) provided on the surface of the inner cylinder and moreover to permit the inner cylinder to move axially and slidably. The outer cylinder, moreover, should have an opening (65) at a place corresponding to an opening (59) provided on the surface of the inner cylinder, through the openings of which the liquid to be tested is allowed to enter or exit with the both cylinders fabricated. Otherwise, the outer cylinder which is devoid of the cylindrical portion corresponding to the opening (59) may suffices, as shown in FIG. 15-(D).

Furthermore th outer cylinder should naturally have, as illustrated in FIGS. 15-(C) and 15-(D), the entirely cylindrical portion H from the end of the inner protective cylinder insertion up to the opening which is longer than the distance G between the sealing means (61), (62).

FIG. 15-(E) shows that the sampler body, the inner cylinder and the outer cylinder, as depicted in FIG. 15-(A), (B) and (C), are fabricated to be ready for measurement. The porous tubing (29), the sealing means (56), (61), (62), the openings (59), (65) are positioned relative to each other as illustrated in the figure, and thus the liquid enters or exits freely to be in contact with the porous tubing (29). On the other hand, the liquid inside the inner cylinder is separated by sealing from the outside by the sealing means (56). The liquid in a space between the inner and outer cylinders and in the container is separated by sealing from the outside by the sealing means (62). If an disorder happens or periodical inspection, washing or replacement of the tubing is carried out during measurement in a state such as depicted in FIG. 15-(E), the inner cylinder holding the sampler body is drawn out until the sealing means (61) comes to the entirely cylindrical portion H. During the drawing out of the inner cylinder, the liquid is sealed from the outside through the sealing means (62). After the drawing out, the liquid in the container is sealed through the sealing means (61) from the outside and the inside of the inner cylinder. Under the situation when the sampler body is removed from the inner cylinder, the liquid in an amount more than accumulated in the inner cylinder flows out by no means because the inside of the inner cylinder is perfectly sealed from the outside through the sealing means (61), thereby operation including inspection, washing, adjustment, replacement and the like of the sampler body being made very feasibly. FIG. 15-(F) shows a state that the sampler body is being removed from the inner cylinder. In this figure the numerals (75), (57) are flanges for determination of the position of the sampler body, the inner and outer cylinders relative to each other.

Shown in FIG. 16 is a sampling means of another structure in which a plurality of porous tubings are provided to the sampling means, and only the porous tubing under measurement is in contact with the liquid, while the other porous tubings being isolated from the liquid, and at the time of emergency or termination of the lifetime of the tubing now in use, one of the other tubings is ready for use in place thereof.

FIG. 16-(A) shows a sampler body holding two porous tubings. One porous tubing (29) connected to the carrier gas supply pipe (47) and the carrier gas discharge pipe (46) is supported by the head holder (72) and the intermediate holder (76), both holders having the sealing means (73), (77) such as an O-ring, another porous tubing (80) connnected to the carrier gas supply pipe (78) and the carrier gas discharge pipe (79) is supported by the intermediate holder (76) and the main holder (44), having likewise the sealing means (56). Each of the holders (72), (76) and (44), as well as the sealing means (73), (77) and (56) should have the same diameter. The distance partitioned by the sealing means, namely between the head holder sealing means (73) and the intermediate holder sealing means (77), and between the intermediate holder sealing means (77) and the main holder sealing means (56) should most suitably be the same. The porous tubings (29), (80) should have the same length, respectively, as influencing the measurement.

FIG. 16-(B) shows a protective cylinder for securing the sampler body to the container filled with the liquid. The protective cylinder (49) is usually installed to the container wall (70). On the surface of the protective cylinder (49) an opening (74) is provided through which the liquid enters to come in contact with the tubing and exits. The length of the opening (74) should be shorter than the foregoing distance partitioned by the sealing means. The inside surface of the protective cylinder (49) is so smooth that the sampler body may be moved axially slidably by a mannual or automatic manner, moreover perfect seal is achieved. The protective cylinder (49) should have the entirely cylindrical portion longer than the distance partitioned by the sealing means (77) provided on the intermediate holder (76) and the sealing means (56) provided on the main holder (44). The full length of the protective cylinder should be longer than the distance between the sealing means (73) on the head holder (72) and the sealing means (56) on the main holder (44). Hereinbelow will be referred to the use of the apparatus.

The sampler body and the protective cylinder should, at the time of measurement, be positioned relative to each other as illustrated in FIG. 16-(C). A first measurement is effected by the porous tubing (29) and thus the carrier gas supply source and the detector are respectively connected to the carrier gas supply pipe (46) and the carrier gas discharge pipe (47). As is apparent from FIG. 16-(C), the liquid comes in contact with the porous tubing (29) through the opening (74). The liquid is completely isolated from the outside through the sealing means (77) provided on the intermediate holder (76). The apparatus is so fabricated that the porous tubing (80) near the main holder (44) is not in contact with the liquid to thus always keep it new, ready for use. When an inconvenience occurs on the porous tubing during measurement, the sampler body is moved axially as indicated in FIG. 16-(D). In this figure the porous tubing (80) is allowed to be in contact with the liquid through the opening (74). Concurrently with the axial movement of the sampler body from the state as shown in FIG. 16-(C) to that in FIG. 16-(D), the line comprising the carrier gas supply pipe (47) and the carrier gas discharge pipe (46), connected to the porous tubing (29) must be shifted to the line comprising the carrier gas supply pipe (78) and the carrier gas discharge pipe (79), connected to the porous tubing (80). Moreover during the axial movement of the sampler body, the sealing means (56) of the main holder is always in airtight contact with the inside surface of the entirely cylindrical portion so that no leakage of the liquid takes place.

The sealing means (73) on the head holder is not necessarily required, if not provided, there is possibility that the difference in measurement or adverse effects might be resulted, because flow of the liquid in contact with the porous tubing differs between the porous tubing (29) near the head holder and the one (80) near the main holder. For the reason the presence of the sealing means (73) is preferred. The shifting of the porous tubing (29) to the porous tubing (80) should desirably be effected instantly and automatically by means of an electromagnetic valve, an automatic cock, a piston, a cylinder and so on, including the shifting of the carrier gas supply or discharge line and the detector. By so doing, continuous measurement is possible without interruption.

Figure 17:
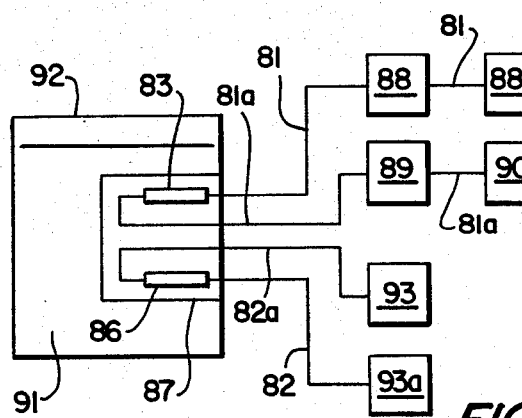
FIG. 17 is a diagram showing a measurement method and apparatus made up of a sampling means having two porous tubing; one for the measurement, the other for standby at the time of emergency.
Figure 16A:
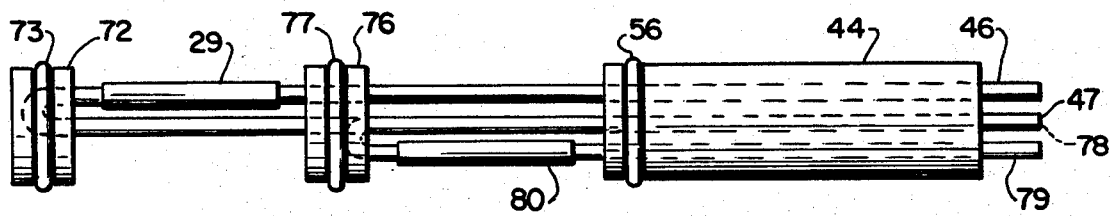
FIG. 16 is a diagram illustrative of a sampling means having two porous tubings, wherein (A) is a sampler body, (B) is a protective cylinder, (C) depicts the use of a first porous tubing and (D) indicates the use of a second porous tubing.
Figure 16B:
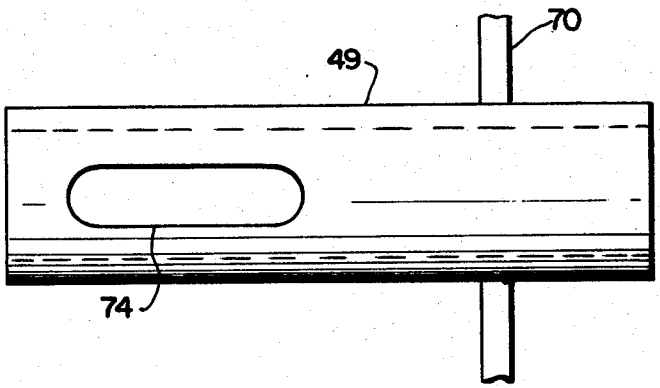
Figure 16C:
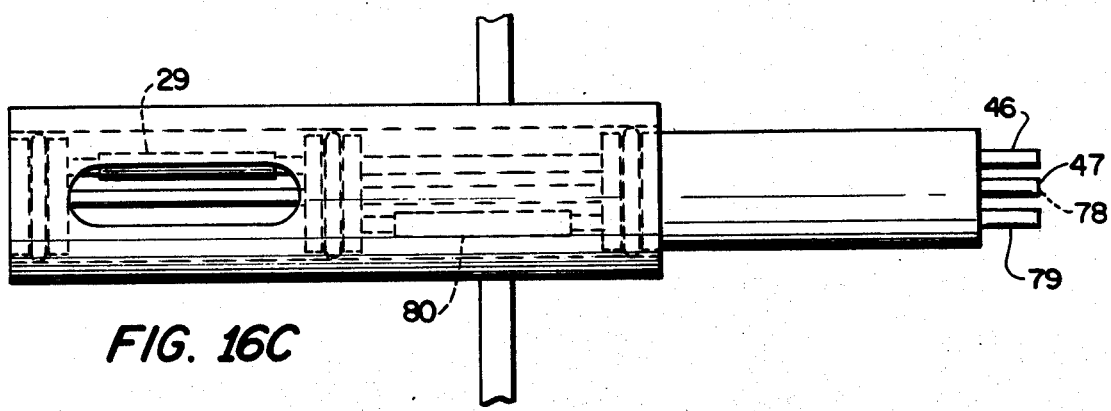
Figure 16D:
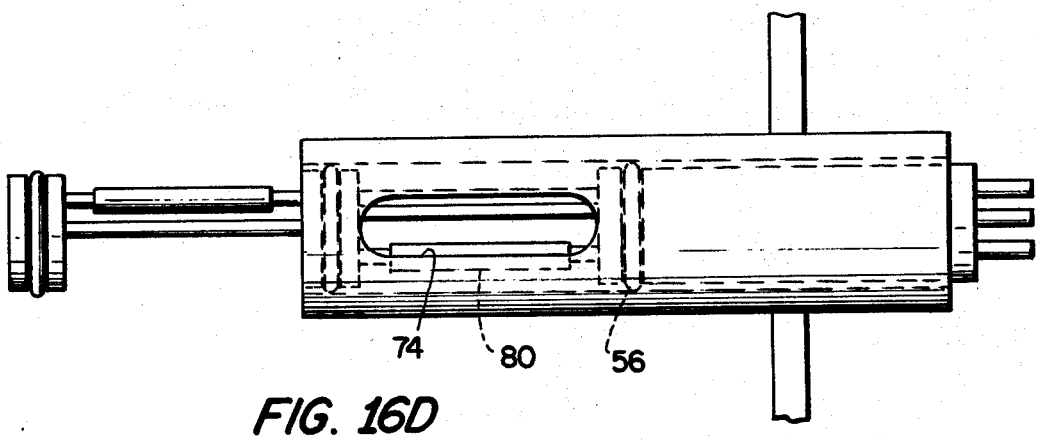

In FIG. 17 there is illustrated an apparatus wherein the sampling means is equipped with a plurality of porous tubings, to one of those tubings the carrier gas is supplied for measurement, the other tubings are kept as standby for ready for use in measurement in case of emergency where the foregoing tubing now in use is out of order or terminated the lifetime, by supplying thereto a compressed gas. In the figure, the case of using two porous tubings is shown.

The sampling means (87) providing two porous tubings (83), (86) is positioned to the container (92) filled with the liquid (91) to be tested. The porous tubings (83), (86) are both in contact with the liquid, one end of the porous tubing (83) is connected through the carrier gas supply pipe (81) and the carrier gas control means (88) to the carrier gas supply source (88a), the other end thereof is connected to the detector (90) through the carrier gas discharge pipe (81a) and the choking means (89). The other porous tubing (86) is connected at each end to the compressed gas supply source (93) through the carrier gas supply pipe (82a), and to the compressed gas discharge outlet (93a) via the carrier gas discharge pipe (82). The compressed gas supply source (93) is capable of supplying the compressed gas with the pressure sufficient to permit it to jet out into the liquid (91) through continuous minute channels of the tubing.

When the lifetime of the porous tubing (83) terminated or an inconvenience occured on that tubing during measurement, supplying of the compressed gas to the porous tubing (86) is discontinued, then the carrier gas is supplied, instead of the compressed gas, by shifting connection of the carrier gas pipe to the carrier gas control means (88) and the choking means (89) from the compressed gas supply source (93) and the compressed gas discharge outlet (93a), whereby the measurement is carried out continuously. It is feasible and desirable that the carrier gas switchover means are provided on the way of the carrier gas pipes (81), (81a), (82) and (82a) to thus facilitate the exchanging of the carrier gas and the compressed gas. It is further possible that immediately before the termination of the lifetime of the porous tubing, the supply of the carrier gas is automatically shifted to a new porous tubing, to thus continue the measurement.

If there is a fear that the volatile substance or steam in the carrier gas condenses in the passageways of the carrier gas, a heating device is needed to keep the temperature of the carrier gas passageway from the porous tubing to the detector not lower than that of the liquid.

The compressed gas, as mentioned earlier, should neither place a bad influence on the liquid nor contain the miscellaneous microorganisms in the case of cultivation processes.

As the material for the parts of the sampling means, metals, synthetic resins, glasses and any other material processable may be selected, among which stainless steel is the most suitable in respect to processability, strength, cost, chemical resistance and the like. As the material for the sealing means, ordinary synthetic rubber series materials are preferred to use but suitable materials having heat resistance, chemical resistance and resiliency may be selectively used, depending on the liquid to be tested and conditions. Butadieneacrylonitrile rubbers (Buna-N), chloroprene rubbers, silicone rubbers, fluorocarbon rubbers are preferred for use. The shape of the sealing means may preferably be an O-shaped ring for sealing of cylindrical bodies.

Additionally in heating up the passageway of the carrier gas to prevent condensation of the volatile substance and steam in the carrier gas, as stated earlier, it is natural that as far as sufficient heat exchange is effected, for instance, like parts of the carrier gas discharge pipe immersed in the liquid under measurement, no specific heating is required.

Figure 22:
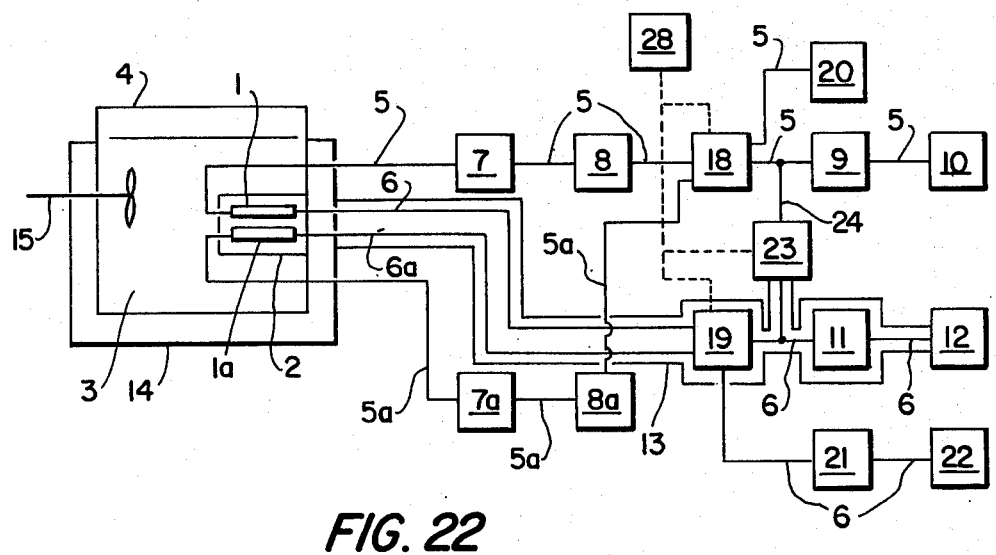
FIG. 22 is a diagram showing a method and apparatus providing a plurality of sampling means for lengthening continuously measurable time, which were added to an apparatus equipped with the sterilization system under heat and pressure.

In FIG. 22, there is shown an apparatus which is equipped with the sampling means (2) providing a plurality of the porous tubings (1), (1a), the compressed gas supply source (20), the carrier gas switchover means (18), (19), the carrier gas switchover controller (28), the bypass line (24), the compressed gas discharge outlet (22) and the like.

The apparatus not only posesses a function of standing sterilization under heat and pressure of the container (4) to which the sampling means (2) is installed, but also posesses a function of enabling long-term continuous measurement over the lifetimes of a plurality of the porous tubings' portion. Basically the apparatus is equivalent to the combined use of the apparatus shown in FIG. 5 and that given in FIG. 17.

The apparatus is fabricated so that by operation of the carrier gas switchover means (18), (19), the compressed gas or the carrier gas is passed through optional one or two of those plural tubings and each gas exiting from the tubings is led to the detector (12) or the compressed gas discharge outlet (22). The structure, specification and the like are the same as stated in FIG. 5 and FIG. 17.

Figure 23:
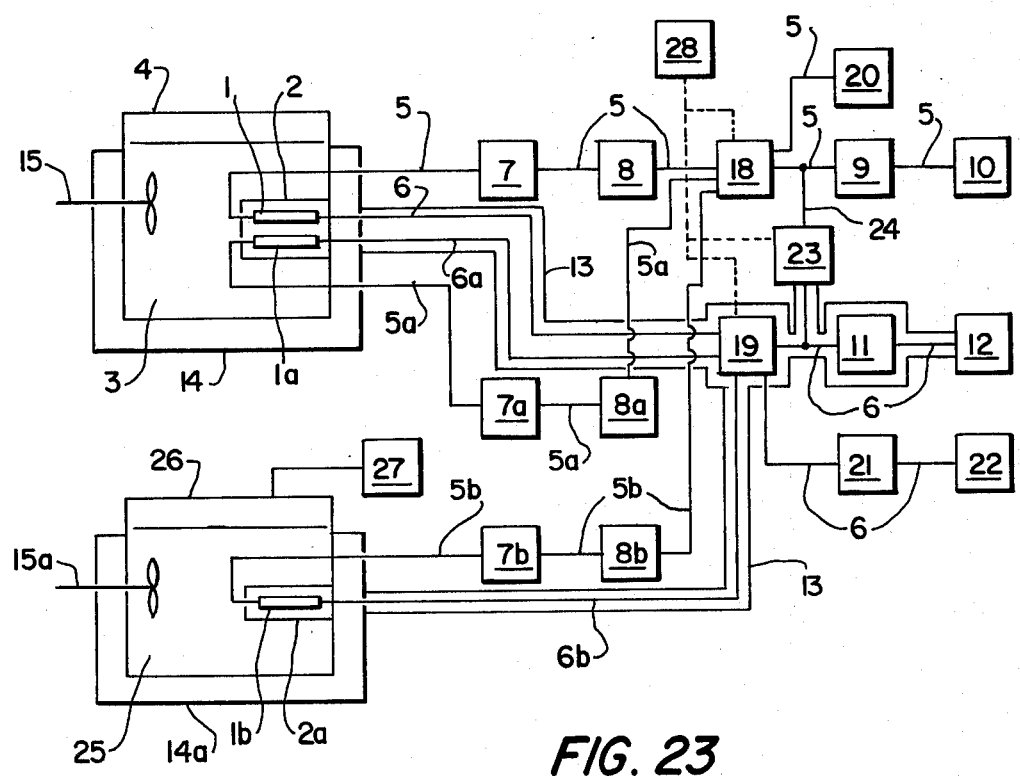
FIG. 23 is a diagram illustrating a method and apparatus in which a plurality of sampling means is provided for lengthening continuously measurable time to an apparatus which is equipped with both sterilization and calibration systems.

Illustrated in FIG. 23 is an apparatus which is capable of calibrating at any time the measured outputs by further adding to the apparatus given in FIG. 22 a second sampling means (2a) in a second container (26) filled with a standard solution containing the volatile substance of a known concentration. The apparatus is basically comprised of the apparatus in FIG. 7 and FIG. 17, or FIG. 6 and FIG. 22.

In this apparatus the carrier gas or the compressed gas is also passed through the porous tubing (1b) of the second sampling means (2a), then introduced to the detector (12) or the compressed gas outlet (22). It is, of course, possible to serve the container (26) as a measurement container by being filled with a liquid to be tested. The particular structure and specification are the same as mentioned in FIG. 6, FIG. 7, FIG. 17 and FIG. 22.

In addition, the structures of the measurement apparatus depicted in FIG. 22 and FIG. 23 are basically the same as shown in FIG. 3, FIG. 5, FIG. 6 and FIG. 7.

Hereinafter, the present invention will be described by way of examples that follow, through which effects and results produced by the present method and apparatus will be made clear.

EXAMPLE 1

Using the apparatus as shown in FIG. 3, the relation between the flow rate and the pressure of the carrier gas passing through the porous tubing was observed.

A porous tubing made of tetrafluoroethylene resin having an average pore size of about 0.45 $\mu$m, a porosity of about 60%, an inside diameter of about 3.0 mm, an outside diameter of about 4.0 mm and a length of about 10 cm was served as the porous tubing (1).

As the carrier gas supply and discharge pipes (5), (6), a metallic pipe made of stainless steel #316 having an inside diameter of about 2.0 mm, an outside diameter of about 3.0 mm and a length of about 300 cm was used.

The carrier gas discharge pipe (6) and the carrier gas choking means (11) were heated up to about 80° C. by the heating device (13).

As the fixed choking means (11), stainless steel pipes having an inside diameter of about 0.3 mm and lengths of about 45, 60 and 75 cm, respectively were used. By operating the carrier gas control means (9), the flow rate ranging from about 30 ml per min to about 50 ml per min was obtained under the pressure ranging from about 0.3 Kg per cm$^2$G to about 0.6 Kg per cm$^2$G, as given in FIG. 2 Nitrogen gas was served as the carrier gas. The carrier gas control means (9) was used which was comprised of a pressure control device an a needle valve.

EXAMPLE 2

In the cultivation process of microorganisms where pressure of the culture liquid at a measuring point varies continuously from about 0.4 Kg per cm$^2$G to about 0.5 Kg per cm$^2$G, continuous measurement of the concentration of ethanol was effected. The interfacial tension of the culture liquid was 37 dyne per cm at the temperature of 30° C.

Using the apparatus as given in FIG. 3, the fixed choking means (11) having an inside diameter of about 0.3 mm and a length of about 60 cm was used and a hydrogen flame ionization detector (manufactured by Shimadzu Seisakusho Ltd.) was served as the gas detector (12). The other conditions were the same as in Example 1. The carrier gas was supplied into the porous tubing at a pressure of about 0.37 Kg per cm$^2$G and at a rate of about 36 ml per min and the concentration of ethanol in the culture broth was measured continuously. Over about 70 hours accurate and stable measurement was conducted.

Figure 18:
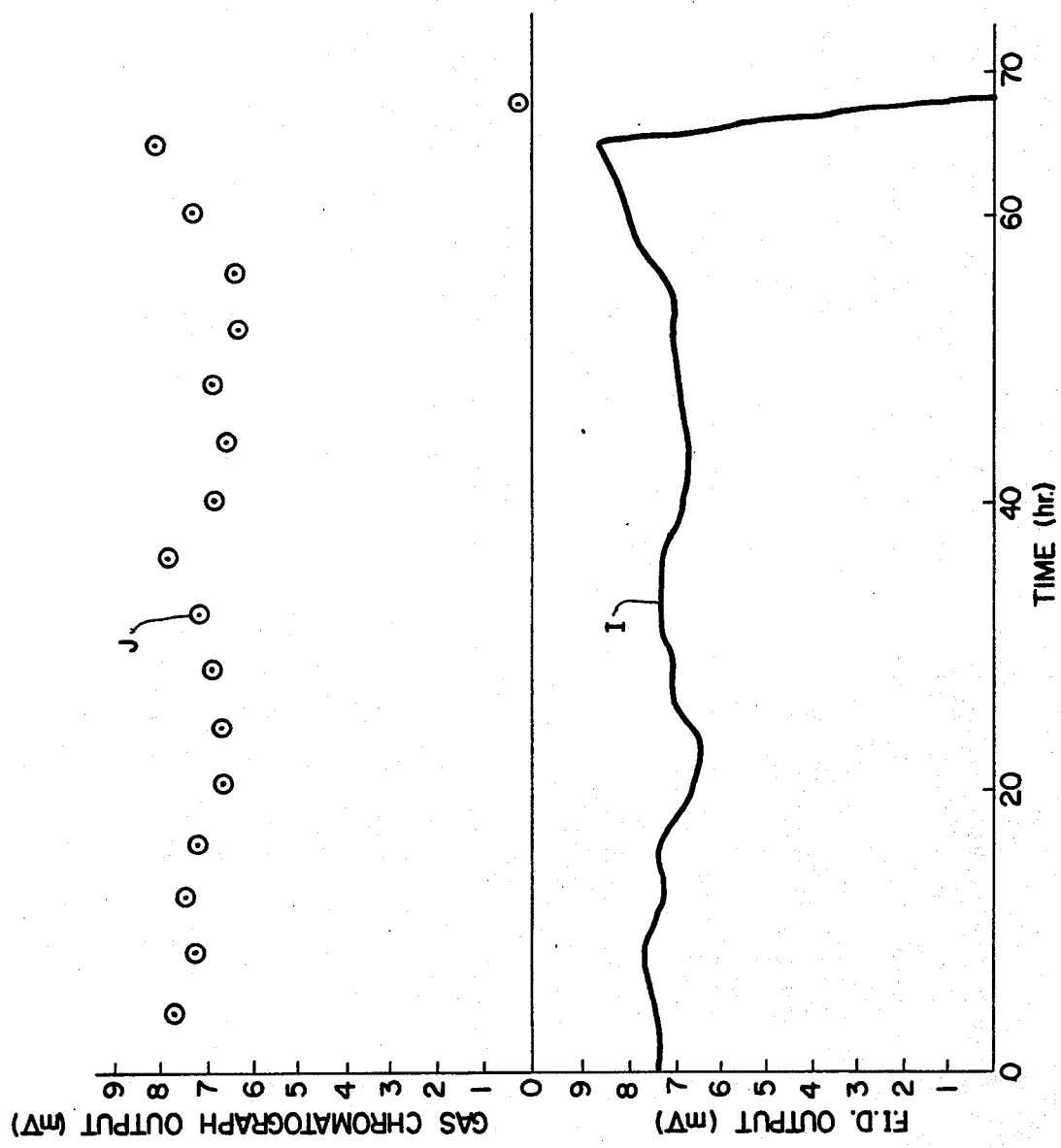
FIG. 18 is a graph indicating output values of the ethanol concentration measured continuously in Example 2 and values obtained by intermittent analysis.

In FIG. 18, I shows the concentration of ethanol obtained by the foregoing continuous measurement, while J shows the concentration of ethanol obtained by intermittent measurement in which the culture broth was taken out, the cells are separated, thereafter ethanol being measured by a gaschromatography.

As obvious from FIG. 18, it is understood that the ethanol concentration measured continuously according to the present invention is accurate, as compared with that obtained by the gaschromatography.

EXAMPLE 3

The apparatus as depicted in FIG. 5 was installed to the fermentor for cultivating the microorganisms as used in Example 2. After sterilizing, prior to cultivation, various detectors and the fermentor by steam under heat and pressure, a series of operations including from sterilization to continuous measuring of ethanol concentration were performed. The porous tubing (1) and the carrier gas supply and discharge pipes (5), (6) were the same as used in Example 1. The carrier gas switchover means (18), (19) were employed which were comprised of two-way electromagnetic valves and three-way electromagnetic valves, permitting almost no residence of the liquid therein. As the switchover means provided on the bypass line the two-way electromagnetic valve was also employed. These electromagnetic valves were constructed so that a desired carrier gas line might be selected with ease by operating one rotary switch. Nitrogen gas was served as the carrier gas and a stainless pipe having an inside diameter of about 0.3 mm was served as the choking means (11). As the detector (12) was a hydrogen flame ionization detector employed, as used in Example 2. The sterilized air was served as the compressed gas and a variable choking means using a needle valve was served as the choking means (21).

The fermentor (4) was sterilized, prior to cultivation, by being maintained for about 5 hours at 120° C. under 1 Kg per cm$^2$G by the use of steam. During sterilization, the compressed gas was supplied through the compressed gas supply source (20) so that pressure and the flow rate might be about 1.2 Kg per cm$^2$ and about 1.5 liters per min, respectively, when passed through the porous tubing (1). During the passage of the compressed gas through the porous tubing, the carrier gas was introduced to the detector (12) via the bypass line (24) and the bypass line switchover means (23) provided thereon.

Figure 19:
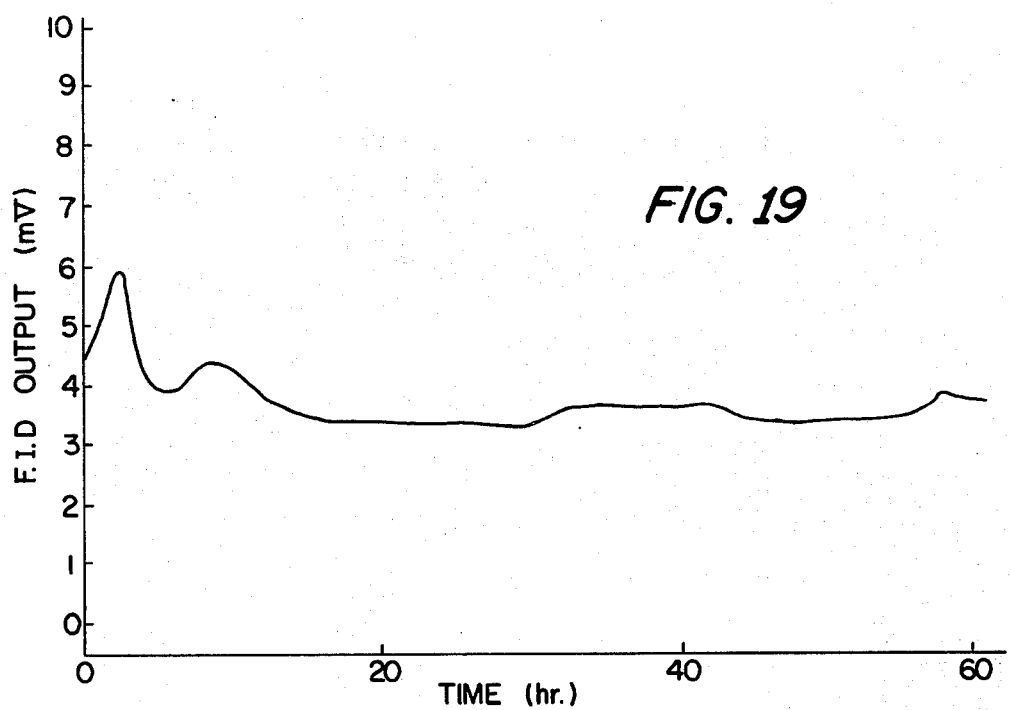
FIG. 19 is a graph showing output values of the ethanol concentration obtained by continuous measurement in Example 3.

After cooling, reduction of pressure of the fermentor and charging of the liquid into the fermentor, cultivation was commenced and continuous measurement of the ethanol concentration in the liquid was begun. Over a long period of time continuous measurement was accomplished with accurate and stable outputs. In FIG. 19, there was given the output measured corresponding to the ethanol concentration. In the above example, the carrier gas discharge pipe, the carrier gas switchover means and the carrier gas choking means were heated up to about 80° C. by a heating device. The carrier gas was passed at a rate of 36 ml per min under 0.37 Kg per cm$^2$G.

EXAMPLE 4

Figure 21:
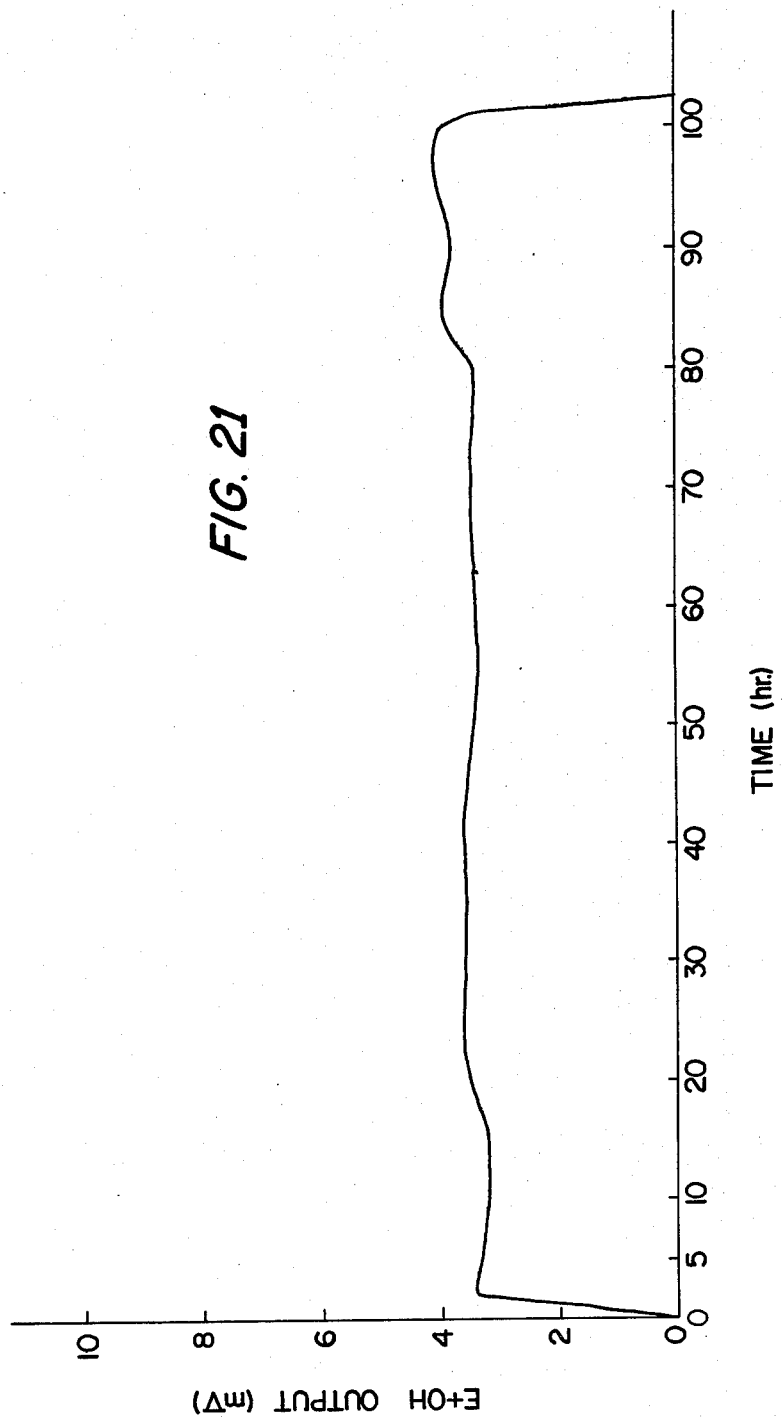
FIG. 21 depicts a graph showing output values of the ethanol concentration measured continuously in Example 4.

A series of operations including from sterilization to measurement were conducted under the same conditions as in Example 3, excepting that cultivation time was prolonged beyond 100 hours. FIG. 21 shows that stably continuous measurement of the ethanol concentration was achieved from commencement of the cultivation to termination thereof.

EXAMPLE 5

The concentrations of ethanol contained in two kinds of liquids were measured reciprocally, using the apparatus as depicted in FIG. 6.

The sampling means (2),(2a), the porous tubings (1),(1a), the carrier gas supply pipes (5),(5a) and the carrier gas discharge pipes (6),(6a) were of the same specification, respectively. The porous tubing and the carrier gas pipes used were the same as used in Example 1.

The cultivation was performed in 2-liter glass beakers (4),(26), which were equipped with not only agitators (15),(15a) having blades in the same shape, operable at the same rate of rotation, but heating devices having the same heating capacity. As the carrier gas choking means (11), a pipe with an inside diameter of about 2.0 mm was used, for resistance to become approximately zero, since the pressure of the liquid imposed on the porous tubing (1) (1a) was extremely small. A fine flow controller was served as the carrier gas control means (9). Nitrogen gas as the carrier gas was supplied at a rate of 40 ml per min so that the pressure might become approximately zero in the vicinity of the porous tubing. The carrier gas discharge pipes, the carrier gas switchover means, the choking means were heated up to 50° C. by heating devices (13). A hydrogen flame ionization detector (manufactured by Shimadzu Seisakusho Ltd.) was used as the detector (12).

Each of the carrier gas switchover means (18), (19) was comprised of two three-way electromagnetic valves and automatically controlled at intervals by a controller (28) ("YEWPACK", manufactured by Yokogawa Electric Works, Limited). The liquids to be measured were a 2% (V/V) aqueous solution containing ethanol (solution K) and a 0.5% (V/V) aqueous solution containing ethanol (solution L), which were controlled at 22.5° C. and agitated at 200 r.p.m. The K and L solutions were reciprocally measured by automatically shifting the carrier gas switchover means at intervals of three minutes. The obtained results were provided in FIG. 8. It is understood from the figure that the output becomes stable within one minute after the shifting of the carrier gas. The outputs were 7.45 mV for K solution and 1.85 mV for L solution, both being very accurate.

EXAMPLE 6

Using the apparatus as used in Example 5, calibration was carried out by comparing the output of a solution of an unknown concentration with that of a solution of a known concentration.

One container (26) was filled with the standard solution comprising a 2% (V/V) aqueous solution (solution K) and the other container (4) was filled with an aqueous solution, the ethanol concentration of which is unknown (solution M). The both solutions were subjected to the same temperature control and stirring.

By operating the carrier gas switchover means (18),(19) by means of the carrier gas switchover controller (28), the standard solution (K) and the solution (M) were measured alternately. The average value of the outputs obtained in the region where those become stable was regarded as the measured output in both solutions. It is possible to know the concentration of the solution (M) of an unknown concentration by multiplying a ratio of the measured output of the solution (M) to that of the standard solution (K) by the concentration of the standard solution (K). The foregoing calculation was allowed to be conducted by the carrier gas switchover controller, then respective average measured outputs of solutions (K) and (M), and the concentration of the solution (M) obtained by calculation were indicated simultaneously.

The both solutions were shifted at intervals of one minute and the outputs obtained after 45 seconds since being shifted were averaged.

At first, the standard solution (K) was measured, then the unknown solution (M) was measured, then the concentration of the solution (M) being calculated. As the standard solution a 2% (V/V) aqueous ethanol solution was used, while an aqueous ethanol solution, the ethanol concentration of which is varied gradually was served as the unknown solution (M).

Figure 20:
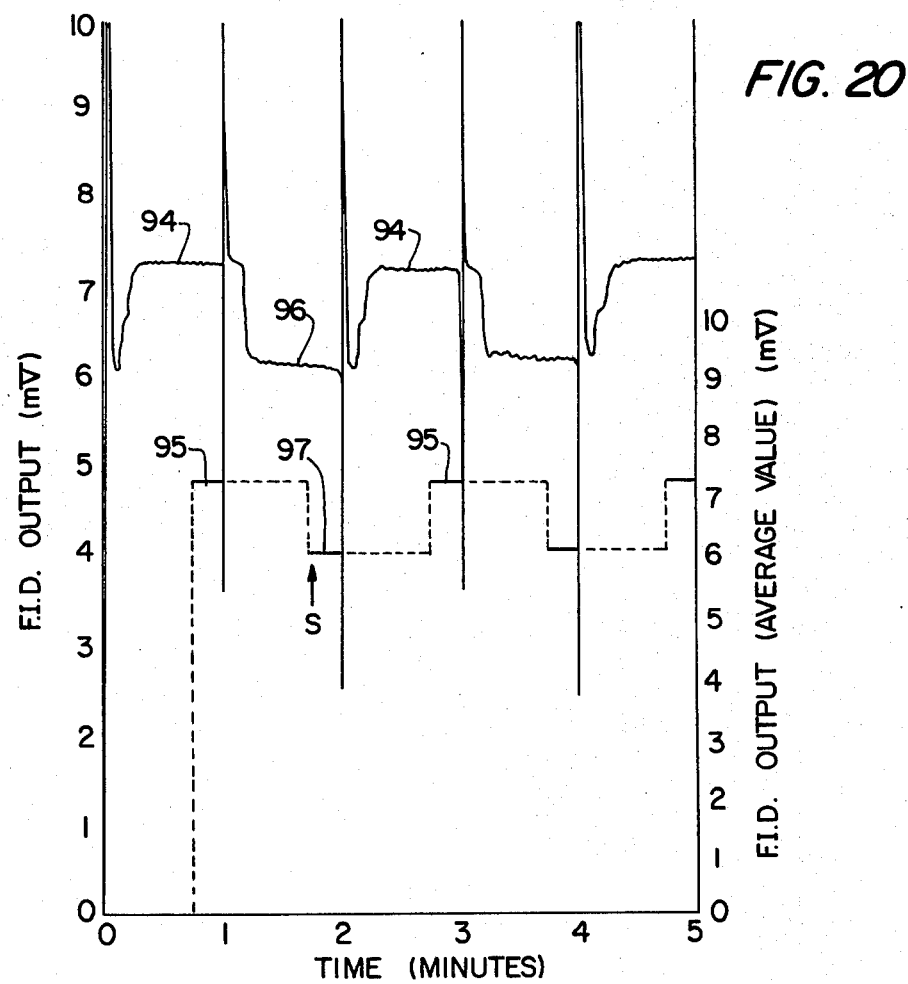
FIG. 20 is a graph showing output values of the ethanol concentration measured for the standard solution and a liquid of an unknown concentration, obtained in calibration in Example 6.

In FIG. 20, the numeral (94) is the output of the standard solution (K), (95) is the average measured output of (K) after being stable (45 seconds after the shifting), (96) is the output of the unknown solution (M) and (97) is the average measured output of (M) after stability (45 seconds after the shifting). The concentration of the unknown solution (M) indicated on the indicator was 1.67% (V/V) to that of the standard solution (K) being 2.0% (V/V). At S point the solution (M) was sampled out and subjected to the measurement by a gaschromatography to thereby obtain 1.65% (V/V). From the comparison of the two, it is apparent that according to the present invention an exceedingly accurate measurement becomes feasible.

What we claim is:

1. A method for measuring the concentration of a gaseous or volatile substance in a liquid comprising the steps of:
    placing at least one porous partition tubing in a container filled with the liquid to immerse the tubing in the liquid, said tubing having liquid repellency and continuous minute channels extending through the partition tubing wall,
    connecting a carrier gas supply source to one end of the tubing through a carrier gas supply pipe and a carrier gas control means, while connecting a gas detector to the other end of the tubing through a carrier gas discharge pipe and a chocking means, and
    introducing to the detector the gaseous or volatile substance passing from the liquid into the carrier gas through the continuous minute channels, while controlling the flow rate and pressure of the carrier gas flowing through the tubing at a predetermined value by operating concurrently both the carrier gas control means and the choking means, whereby the concentration of the substance is measured the pressure of the carrier gas being controlled so that the pressure difference $\Delta P$ between the liquid and the carrier gas at respective sides of the porous partition tubing wall may be Kg per $cm^2$ or below when the liquid has an interfacial tension $\sigma$ of about 25 to about 37 dyne per cm and the average pore size is R $\mu m$, and Kg per $cm^2$ or below when the interfacial tension $\sigma$ exceeds about 37 dyne per cm, thus the carrier gas being supplied at a predetermined flow rate.

2. A method of claim 1, wherein the container filled with the liquid is sterilized by switching a first carrier gas switchover means at the downstream of the carrier gas control means and a second carrier gas switchover means at the upstream of the choking means to discontinue the supply of the carrier gas to the porous tubing to introduce the carrier gas into the gas detector through a bypass line provided between the carrier gas supply pipe and the choking means, supplying to the tubing a compressed gas through a compressed gas supply source connected to the first carrier gas switchover means, said compressed gas having a pressure higher than that of the container at a flow rate enough to discharge steam permeating into the carrier gas through the porous partition tubing wall, then discharging the compressed gas passing through the porous partition tubing containing a large quantity of steam through the carrier gas discharge pipe, the choking means connected to the second carrier gas switchover means and the compressed gas discharge outlet, whereby the container is sterilized by steam under heat and pressure.

3. A method of claim 1, wherein calibration is carried out by providing a second porous partition tubing having liquid repellency and continuous minute channels extending through the partition tubing wall which is placed in a calibration container filled with a standard solution having a known concentration of a gaseous or volatile substance, said standard solution having a temperature and a pressure which are equal to those of the liquid to be tested, connecting both ends of the second porous partition tubing to the first and second carrier gas switchover means, respectively, through the carrier gas supply pipe and the carrier gas discharge pipe, then introducing the carrier gas passed through the second porous partition tubing to the gas detector, whereby sensitivity of the method is calibrated.

4. A method of claim 1, wherein the container filled with the liquid is sterilized by switching a first carrier gas switchover means at the downstream of the carrier gas control means and a second carrier gas switchover means at the upstream of the choking means to discontinue the supply of the carrier gas to the porous tubing to introduce the carrier gas into the gas detector through the bypass line provided between the carrier gas supply pipe and the choking means, supplying to the tubing the compressed gas through the compressed gas supply source connected to the first carrier gas switchover means, said compressed gas having a pressure higher than that of the container at a flow rate enough to discharge steam permeating into the carrier gas through the porous partition tubing wall, then discharging the compressed gas passing through the porous partition tubing containing a large quantity of steam through the carrier gas discharge pipe, the choking means connected to the second carrier gas switchover means and the compressed gas discharge means, to thereby effecting the sterilization of the container, and moreover, calibration is carried out by providing a second porous partition tubing having liquid repellency and continuous minute channels extending through the partition tubing wall which is placed in the calibration container filled with a standard solution having a known concentration of a gaseous or volatile substance, said standard solution having a temperature and a pressure which are equal to those of the liquid to be measured, connecting both ends of the second porous partition tubing to the first and second carrier gas switchover means, respectively, through the carrier gas supply and discharge pipes, then introducing the carrier gas passed through the second porous partition tubing to the gas detector, to thereby effecting the calibration of the method.

5. A method of claim 1, wherein at least one standby porous partition tubing having liquid repellency and continuous minute channels extending through the partition tubing wall is included, a carrier gas supply pipe is connected to one end of the standby porous partition tubing and a carrier gas discharge pipe is connected to the other end thereof, a compressed gas is supplied through the carrier gas supply pipe into the standby porous partition tubing to allow the compressed gas to jet out into the liquid through the continuous minute channels so that standby porous partition tubing may be kept ready for use in measuring the concentration of the substance for emergency of the porous partition tubing now in use.

6. A method of claim 1, wherein the porous partition tubing is made of tetrofluoroethylene resin having an average pore size of about 0.1 to about 1.0 μm and a porosity of about 20 to about 80%.

7. A method of claim 1, wherein the pressure of the carrier gas is controlled so that the pressure difference ΔP may be [0.05.σ−1.05] Kg per cm² or below when the porous partition tubing made of tetrafluoroethylene resin having a porosity of about 45 to about 60%, an average pore size of about 0.4 to about 0.6 μm and a thickness of about 400 to about 600 μm is used and the liquid has an interfacial tension σ of about 25 to about 37 dyne per cm, and [0.0143.σ+0.27] Kg per cm² or below when the interfacial tension σ exceeds about 37 dyne per cm, thus the carrier gas being supplied at a predetermined flow rate.

8. A method of claim 7, wherein the pressure of the carrier gas is controlled so that the pressure difference ΔP may be [0.56.σ−1.45] Kg per cm² or below when the liquid has an interfacial tension σ of about 29 to about 37 dyne per cm, and [0,0143.σ−0,129] Kg per cm² or below when the interfacial tension exceeds about 37 dyne per cm.

9. An apparatus for measuring the concentration of a gaseous or volatile substance in a liquid comprising:
a sampling means including a porous partition tubing made of tetrafluoroethyline resin and having liquid repellency and continuous minute channels extending through the porous partition tubing wall, the porous partition tubing having an average pore size of about 0.1 to about 1.0 μm and a porosity of about 20 to about 80%.

10. An apparatus of claim 9, wherein the sampling means further includes at least one standby porous partition tubing having liquid repellency and continuous minute channels extending through the partition tubing wall, to respective ends of which tubing a carrier gas supply pipe and a carrier gas discharge pipe are connected, and the porous partition tubing is connected to a compressed gas supply source.

11. An apparatus of claim 9 or claim 10, wherein the sampling means further includes a temperature detector incorporated thereinto for detecting the temperature of the liquid.

12. An apparatus of claim 9 or claim 10, wherein the sampling means further includes a protective cylinder which accommodates the temperature detector therein releasably to isolate it from the liquid.

13. An apparatus of claim 9 or claim 10, wherein the sampling means is of a double-cylinder construction comprising:
(A) a sampler body which holds the porous partition tubing having liquid repellency and continuous minute channels extending through the partition tubing wall, on the main holder of which a sealing means is provided which is slidably inserted and removed in an inner cylinder,
(B) an inner cylinder having an opening for measurement incased in an outer cylinder, said inner cylinder being closed at one end and opend at the other end and having a pair of sealing means provided on the opposite sides of the opening which are in airtight contact with the inner surface of the outer cylinder, and
(C) an outer cylinder having an opening for measurement and an entirely cylindrical portion, the length of which is longer than the distance between the two sealing means provided on the inner cylinder.

14. An apparatus of claim 13, wherein the sealing means is an O-ring.

15. An apparatus of claim 9 or claim 10, wherein said sampling means comprising:
(A) a sampler body comprising a main holder having a sealing means and holding the porous partition tubing, a plug having a sealing means, a head holder connected to the plug axially releasably, and the porous partition tubing, and
(B) a protective cylinder accommodating the sampler body therein and having an entirely cylindrical portion, the length of which is longer than the distance between the two sealing means, said protective cylinder having an opening for measurement which is shorter than the distance between the two sealing means, whereby the sampler body (A) is incased axially slidably in the protective cylinder while the two sealing means are in airtight contact with the inner surface of the protective cylinder.

16. An apparatus of claim 15, wherein the sealing means is an O-ring.

17. An apparatus of claim 9 or claim 10, wherein the sampling means comprises;
   a sampler body in which the opposite ends of each of a plurality of the porous partition tubings are held by adjacent holders, each holder having sealing means, and
   a protective cylinder having an opening for measurement shorter than any distance between sealing means provided on the adjacent holders whereby the sampler body is incased axially slidably in the protective cylinder.

18. An apparatus of claim 17, wherein the sealing means is an O-ring.

19. An apparatus of claim 9 or claim 10, wherein the sampling means is of a double-cylinder construction comprising:
   (A) a sampler body holding the porous partition tubing having liquid repellency and continuous minute channels extending through the porous tubing wall, on the main holder of which a sealing means is provided which is slidably inserted and removed in an inner cylinder,
   (B) an inner cylinder having an opening for measurement incased in an outer cylinder, said inner cylinder being open at least at one end and having a pair of sealing means provided on the opposite sides of the opening which are in airtight contact with the inner surface of the outer cylinder,
   (C) an outer cylinder accommodating the inner cylinder having an opening for measurement and a sealing means of the vicinity of the inlet for inserting the inner cylinder, whereby both of inner and outer cylinders are movable relative to each other to thus enable variations in the size of the opening for measurement formed by the overlapped openings.

20. An apparatus of claim 19, wherein the sealing means is an O-ring.

21. An apparatus of claim 9 or claim 10, wherein the sampling means comprises a sampler body holding the porous partition tubing, and a protective cylinder having two openings, one being relatively smaller than the other, in the vicinity of each end of the tubing, and said sampling means is obliquely positioned in the liquid so that the liquid and air bubbles contained in the protective cylinder may flow smoothly along the porous partition tubing.

22. An apparatus of claim 9 or claim 10, wherein a connected portion of the porous partition tubing to the carrier gas supply pipe and the carrier gas discharge pipe, respectively, and the vicinity of the connected portion are reinforced.

23. An apparatus of claim 22, wherein the connected portion is covered with a tube to be in a double-walled tubular construction.

24. An apparatus of claim 22, wherein connected portion is coated with a synthetic resin.

25. An apparatus of claim 22, wherein the connected portion is covered with a tape or film.

26. An apparatus of claim 22, wherein the reinforced portion of the porous partition tubing is molded by a synthetic resin.

27. An apparatus of claim 9 or claim 10, wherein the porous partition tubing has a smaller pore size and/or a lower porosity at both ends and in the vicinity thereof, to which the carrier gas supply pipe and the carrier gas discharge pipe are connected, respectively, than in any other portion, or said tubing is devoid of any continuous minute channels extending through partition tubing wall or any pore at the both ends and the vicinity of the porous partition tubing.

28. An apparatus of claim 27, wherein the porous partition tubing has a porosity of about 30% or below at both ends and in the vicinity thereof to which the carrier gas supply and discharge pipes are connected, respectively.

29. An apparatus of claim 27, wherein the porous partition tubing has a pore size of about 0.2 μm or below at both ends and in the vicinity thereof to which the carrier gas supply and discharge pipes are connected, respectively.

30. An apparatus of claim 9 or claim 10, wherein each of the carrier gas supply and discharge pipes has one connecting edge for connection to one of the ends of the porous partition tubing, said connecting edge having an outer diameter equal to or slightly larger than the inside diameter of the porous partition tubing, wherein the connected portion by inserting said connecting edge into the porous partition tubing is covered with a heat-contractible tube and thermally contracted.

31. An apparatus of claim 30, wherein the porous partion tubing, the both ends of which were reinforced beforehand is employed.

32. An apparatus of claim 9 or claim 10, wherein the porous partition tubing is connected to each of the carrier gas supply and discharge pipes, in which the carrier gas pipe having at one end a screw portion and a connecting edge projecting or being separated from the screw portion, said connecting edge having an outside diameter smaller than that of the screw portion, and equal to or slightly larger than the inside diameter of the porous partition tubing, is inserted into the porous tubing to permit the end of the porous partition tubing to overlap the connecting edge, a ring is put over the tubing and a box nut being secured to the screw portion.

33. An apparatus of claim 9 or claim 10, wherein a silicone series sealant is applied to the connecting portion of the carrier gas supply or discharge pipe and to a space between the pipe and the porous partition tubing, and moreover, the connected portion is covered with a heat-contractible tube and thermally contracted.

34. An apparatus of claim 9, wherein the choking means comprises a pipe having a very small diameter.

35. An apparatus of claim 9, wherein the choking means comprises a plurality of pipes having very small different diameters and different lengths, and a switch-over means for shifting one to another.

36. An apparatus of claim 9, wherein the choking means comprises a variable choking means permitting a continuous variation in choking degree.

37. An apparatus of claim 9, wherein a heating device is provided around the passageway of the carrier gas from the outlet of the porous partition tubing to the inlet of the detector, excepting a portion immersed in the liquid under measurement.

38. An apparatus for measuring the concentration of a gaseous or volatile substance in a liquid comprising:

a sampling means comprising a porous partition tubing made of tetrafluoroethylene resin having a pore size of about 0.1 to about 1.0 μm and a porosity of about 20 to about 80%, and carrier gas supply and discharge pipes, a carrier gas supply means comprising a carrier gas supply source and a carrier gas control means, a compressed gas supply source, a first switchover means, to one end of which the carrier gas supply means and the compressed gas supply source are connected in parallel, and to the other end of which one end of the porous partition tubing is connected through the carrier gas supply pipe, a carrier gas choking means fabricated of a pipe having a small inside diameter connected to a gas detector, a compressed gas choking means connected to a compressed gas discharge outlet, a second switchover means, to one end of which the carrier gas choking means and the compressed gas choking means are connected in parallel, to the other end of which the other end of the porous partition tubing is connected through the carrier gas discharge pipe, a carrier gas bypass line providing a switchover means, for connecting the carrier gas supply line to the carrier gas choking means, and a heating device provided around passageway of the carrier gas from the outlet of the porous partition tubing to the inlet of the gas detector.

39. An apparatus for measuring the concentration of a gaseous or volatile substance in a liquid comprising:

a pair of sampling means comprising porous partition tubings made of tetrafluoroethylene resin having a pore size of about 0.1 to about 1.0 μm, and a porosity of about 20 to about 80%, and carrier gas supply and discharge pipes, a carrier gas supply means comprising a carrier gas supply source and a carrier gas control means, a calibration container providing a pressure control device, a temperature control device, an agitator and one of the sampling means, a first switchover means, to one end of which the carrier gas supply means is connected, and to the other end of which the pair of porous partition tubings are connected, respectively, through the carrier gas supply pipes, a carrier gas choking means fabricated of a pipe having a small inside diameter connected to a gas detector, a second switchover means, to one end of which the carrier gas choking means is connected, and to the other end of which the pair of porous partition tubings are connected in parallel through the carrier gas discharge pipes, a heating device provided around the passageways of the carrier gas from the outlets of the porous partition tubings to the inlet of the gas detector, and a carrier gas switchover controller for automatic shifting of the first and the second switchover means.

40. An apparatus for measuring the concentration of a gaseous or volatile substance in a liquid comprising:

a pair of sampling means comprising porous partition tubings made of tetrafluoroethylene resin having a pore size of about 0.1 to about 1.0 μm and a porosity of about 20 to about 80%, and carrier gas supply and discharge pipes, a carrier gas supply means comprising a carrier gas supply source and a carrier gas control means, a compressed gas supply source, a calibration container providing a pressure control device, a temperature control device, an agitator and one of the sampling means, a first carrier gas switchover means, to one end of which the carrier gas supply means and the compressed gas supply source are connected in parallel, and to the other end of which the pair of porous partition tubings are connected in parallel through the carrier gas supply pipes, a carrier gas choking means fabricated of a pipe having a small inside diameter connected to a gas detector, a compressed gas choking means connected to a compressed gas discharge outlet, a second switchover means, to one end of which the carrier gas choking means and the compressed gas choking means are connected in parallel, and to the other end of which the pair of porous partition tubings are connected in parallel through the carrier gas discharge pipes, a carrier gas bypass line, providing a switchover means, connecting the carrier gas supply means to the carrier gas choking means, a heating device provided around the passageways of the carrier gas from the outlets of the porous tubings to the inlet of the gas detector, and a carrier gas switchover controller for automatic shifting of the first and the second switchover means, and the switchover means on the carrier gas bypass line.

41. An apparatus for measuring the concentration of a gaseous or volatile substance in a liquid comprising:

a sampling means comprising a plurality of porous partition tubings made of tetrafluoroethylene resin having a pore size of about 0.1 to about 1.0 μm and a porosity of about 20 to about 80%, and carrier gas supply and discharge pipes, a carrier gas supply means comprising a carrier gas supply source and a carrier gas control means, a compressed gas supply source, a first carrier gas switchover means, to one end of which the carrier gas supply means and the compressed gas supply source are connected in parallel, and to the other end of which the pair of porous partition tubings are connected in parallel through the carrier gas supply pipes, a carrier gas choking means fabricated of a pipe having a small inside diameter connected to a gas detector, a compressed gas choking means connected to a compressed gas discharge outlet, a second carrier gas switchover means, to one end of which the carrier gas choking means and the compressed gas choking means are connected in parallel, and to the other end of which the pair of porous partition tubings are connected in parallel through the carrier gas discharge pipes, a carrier gas bypass line, including a switchover means, connecting the carrier gas supply means to the carrier gas choking means, a heating device provided around the passageways of the carrier gas from the outlets of the porous partition tubings to the gas detector, and a carrier gas switchover controller for automatic shifting of the first and second switchover means, and the switchover means on the carrier gas bypass pine.

42. An apparatus for measuring the concentration of a gaseout or volatile substance in a liquid comprising:

a first sampling means comprising at least two porous partition tubings made of tetrafluoroethylene resin having a pore size of about 0.1 to 1.0 μm and a porosity of about 20 to about 80%, and carrier gas supply and discharge pipes, a second sampling means comprising a porous partition tubing having the same specification as aforesaid, and carrier gas supply and discharge pipes, a carrier gas supply means comprising a carrier gas supply source and a carrier gas control means, a compressed gas supply source, a calibration container providing a pressure control device, a temperature control device, an agitator and the second sampling means, a first carrier gas switchover means, to one end of which the carrier gas supply means and the compressed gas supply source are connected in parallel, and to the other end of which at least three porous partition tubings are connected in parallel through the carrier gas supply pipes, a carrier gas choking means fabricated of a pipe having a small inside diameter connected to a gas detector, a compressed gas choking means connected to a compressed gas discharge outlet, a second carrier gas switchover means, to one end of which the carrier gas choking means and the compressed gas choking means are connected in parallel, and to the other of which at least three porous partition tubings are connected in parallel through the carrier gas discharge pipes, a carrier gas bypass line, providing a switchover means, connecting the carrier gas supply means to the carrier gas choking means, a heating device provided around the passageways of the carrier gas from the outlets of the porous partition tubings to the inlet of the gas detector, and a carrier gas switchover controller for automatic shifting of the first and the second switchover means, and the switchover means on the carrier gas bypass line.

* * * * *